(12) United States Patent
Moszner et al.

(10) Patent No.: US 9,040,602 B2
(45) Date of Patent: May 26, 2015

(54) DENTAL MATERIALS ON THE BASIS OF HIGHLY ACIDIC POLYMERIZABLE BISPHOSPHONIC ACIDS

(71) Applicant: Ivoclar Vivadent AG, Schaan (LI)

(72) Inventors: Norbert Moszner, Mauren (LI); Yohann Catel, Sargans (CH); Jörg Angermann, Sargans (CH); Thorsten Bock, Tosters (AT); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 13/981,971

(22) PCT Filed: Dec. 6, 2012

(86) PCT No.: PCT/EP2012/074715
§ 371 (c)(1),
(2) Date: Jul. 26, 2013

(87) PCT Pub. No.: WO2013/083734
PCT Pub. Date: Jun. 13, 2013

(65) Prior Publication Data
US 2014/0296364 A1  Oct. 2, 2014

(30) Foreign Application Priority Data
Dec. 6, 2011 (EP) .................... 11192246

(51) Int. Cl.
*C08F 2/46* (2006.01)
*C08G 61/04* (2006.01)
*A61K 6/083* (2006.01)
*A61K 6/00* (2006.01)

(52) U.S. Cl.
CPC ............ *A61K 6/0835* (2013.01); *A61K 6/0023* (2013.01); *A61K 6/083* (2013.01)

(58) Field of Classification Search
CPC ... A61K 6/0835; A61K 6/0023; A61K 6/083; C08L 33/08; C08L 33/10; C08L 33/12
USPC ......................... 522/171, 1; 520/1
See application file for complete search history.

(56) References Cited

U.S. PATENT DOCUMENTS

| | | | |
|---|---|---|---|
| 6,172,131 B1 * | 1/2001 | Moszner et al. | 523/116 |
| 6,512,068 B1 * | 1/2003 | Nakatsuka | 526/277 |
| 6,710,149 B2 | 3/2004 | Moszner et al. | |
| 6,900,251 B2 | 5/2005 | Moszner et al. | |
| 2002/0016384 A1 | 2/2002 | Moszner et al. | |
| 2003/0167968 A1 | 9/2003 | Erdmann et al. | |
| 2004/0077754 A1 | 4/2004 | Moszner et al. | |
| 2004/0206932 A1 | 10/2004 | Abuelyaman | |

FOREIGN PATENT DOCUMENTS

| | | |
|---|---|---|
| DE | 273 846 A1 | 11/1989 |
| DE | 199 18 974 A1 | 12/1999 |
| EP | 0 909 761 A1 | 4/1999 |
| EP | 1 057 468 A1 | 12/2000 |
| JP | 2006-298771 | * 11/2006 |
| JP | 2006-298771 A | 11/2006 |
| WO | 03013444 A1 | 2/2003 |

OTHER PUBLICATIONS

Takase et al, JP 2006-298771 Machine Translation, Nov. 2006.*
Houben-Weyl, Methoden der organischen Chemie, Makromolekulare Stoffe, pp. 1300-1312.
Moszner, N., et al., Chemical aspects of self-etching enamel-dentin adhesives: A systematic review, Dental Materials, Oct. 2005, vol. 21, Issue 10, pp. 895-910.
Francis, M., et al., Diphosphonates Inhibit Formation of Calcium Phosphate Crystals in vitro and Pathological Calcification in vivo, Sep. 19, 1969, Science, vol. 165, pp. 1264-1266.
Catel, Y., et al., Synthesis, Photopolymerization, and Adhesive Properties of New Bisphosphonic Acid Monomers for Dental Application,Journal of Polymer Science: Part A: Polymer Chemistry, Sep. 10, 2009, vol. 47, pp. 5258-5271.
Moszner, N., et al., Monomers for adhesive polymers, 2. Synthesis and radical polymerisation of hydrolytically stable acrylic phosphonic acids, Macromol. Chem, Phys., Apr. 21, 1999, vol. 200, Issue 5, pp. 1062-1067.
Mou, L., et al., Synthesis of a hydrophilic phosphonic acid monomer for dental materials, Chem. Commun., Feb. 21, 2000, pp. 345-346.
Sibold, N., et al., Synthesis and characterization of (co)polymers containing a phosphonate function for use in dental composites, Dec. 2002, Polymer, vol., 43, issue 26, pp. 7257-7267.
Sahin, G., et al., Synthesis and Evaluation of New Dental Monomers with Both Phosphonic and Carboxylic Acid Functional Groups, Journal of Polymer Science Part A: Polymer Chemistry, Feb. 25, 2009, vol. 47, Issue 7, pp. 1953-1965.
Becker HGO, Organikum, 2004, D.2. Nucleophile Substitution am gesättigten Kohlenstoffatom, Wiley-VCH Verlag, Weinheim, pp. 246-247.
Freeman, S., et al., Synthesis and Hydrolosys Studies of Phosphonopyruvate, Jan. 1, 1991, J. Chem. Soc. Perkin Trans. 2, pp. 263-267.
Phillips, A., et al., Phosphonic Systems. 7. Reactions of 2, 3-Epoxyphosphonates with Nucleophiles: Preparation of 2, 3-Disubstituted Alkylphosphonic Esters and Related Systems, Phosphorus, Sulfur, and Silicon, 1992, vol. 71, pp. 165-174.

* cited by examiner

*Primary Examiner* — Ling Choi
*Assistant Examiner* — Jessica E Whitely
(74) *Attorney, Agent, or Firm* — Ann M. Knab; Thad McMurray

(57) ABSTRACT

The invention relates to a dental material which comprises a polymerizable bisphosphonic acid of Formula I:

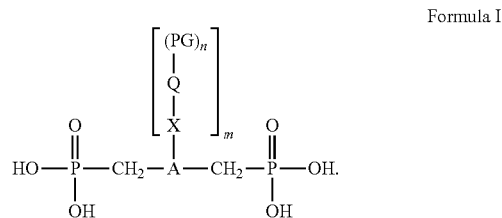

Formula I

The invention also relates to the use of a polymerizable bisphosphonic acid of Formula I for the preparation of a dental material and in particular for the preparation of an adhesive, cement or composite.

43 Claims, No Drawings

DENTAL MATERIALS ON THE BASIS OF HIGHLY ACIDIC POLYMERIZABLE BISPHOSPHONIC ACIDS

CROSS-REFERENCE TO RELATED APPLICATIONS

This application is a National Stage of International patent application PCT/EP2012/074715, filed on Dec. 6, 2012, which claims priority to European patent application No. 11192246.4 filed on Dec. 6, 2012, the disclosures of which are incorporated herein by reference in their entirety.

The present invention relates to polymerizable bisphosphonic acids and their use as monomer components in adhesive dental materials and in particular for the preparation of dental adhesives, cements and composites.

Polymerizable phosphonic acids are important in polymer chemistry and engineering predominantly as co-monomers and allow for the preparation of organic polymers with better thermal stability, improved adhesion properties, reduced flammability and improved solubility in polar solvents. In this context, numerous monomeric phosphonic acids with polymerizable vinyl, dienyl, allyl or styryl groups have been synthesized and polymerized (cf. Houben-Weyl, Methoden der Organischen Chemie, volume E 20 ($2^{nd}$ part), G. Thieme Verlag, Stuttgart-New York 1987, 1300 et seq.). Polymerizable phosphonic acids are also known as components of dental adhesives (cf. N. Moszner, U. Salz, J. Zimmermann, Dental Materials 21 (2005) 895-910) and the subject of numerous patents, such as e.g. DE 100 18 968 C1, DE 102 34 326 B3, DE 199 18 974 A1, EP 1 057 468 A1 and EP 1 169 996 A1.

Bisphosphonic acids (BPA) wherein two phosphonate groups are bonded via a methylene group have been used for many years as diagnostic or therapeutic medicaments in bone or calcium metabolism diseases. For example, alendronic acid is used for treating osteoporosis. It has already been known for a long time (cf. M. D. Francis et al., Science 165 (1969) 1264-1266) that bisphosphonates inhibit the formation of calcium phosphate with the result that bisphosphonates were used in toothpastes to reduce subgingival calculus formation.

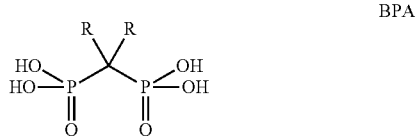

BPA

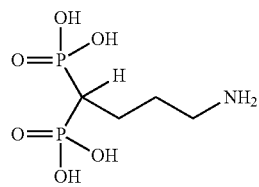

AA

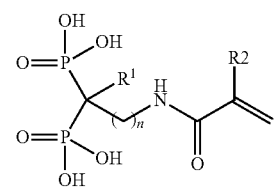

NABPA

Polymerizable N-acryl-aminoalkyl bisphosphonic acids (NABPA) are described in DD 273 846 A1 as a component of adhesion promoters. Analogous methylene bisphosphonic acid (meth)acrylamides are described in WO 2004/060327 A1 as a component of self-etching primers. Such methylene bisphosphonic acids are mainly solids which, although they dissolve excellently in water, are scarcely soluble in organic solvents. Methylene bisphosphonic acid acrylamides with improved solubility were synthesized for dental adhesives by Y. Catel, M. Degrange, L. L. Pluart, P.- J. Madec, T.- N. Phan, F. Chen, W. D. Cook (J. Polym. Sci.: Part A: Polym. Chem. 47 (2009) 5258-5271). WO 03/013444 A1 describes self-etching primers based on bisphosphonic acids with two polymerizable (meth)acrylamide groups, wherein in each case the phosphonic acid groups are bonded, directly or via spacers, to the nitrogen atoms of the (meth)acrylamide groups and these nitrogen atoms are in turn bonded to one another via a further spacer. These compounds are characterized by reduced radical polymerizability. Finally, some aromatic bisphosphonic acids are known which carry two polymerizable methacryl groups, e.g. BPA-1 (N. Moszner, Macromol. Chem. Phys. 200 (1999) 1062-1067) and BPA-2 (L. Mou, G. Singh, J. W. Nicholson, Chem. Commun. 2000, 345-346; N. Sibold, P.- J. Madec, S. Masson, T.- N. Phan, Polymer 43 (2002) 7257-7267; G. Sahin, A. Z. Albayrak, Z. S. Bilgici, D. Avci, J. Polym. Sci.: Part A: Polym. Chem. 47 (2009) 1953-1965).

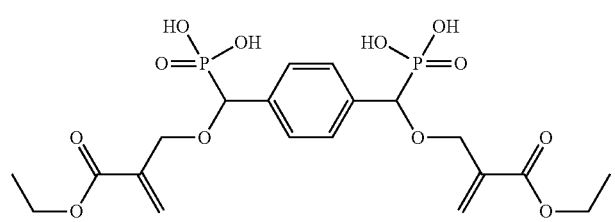

BPA-1

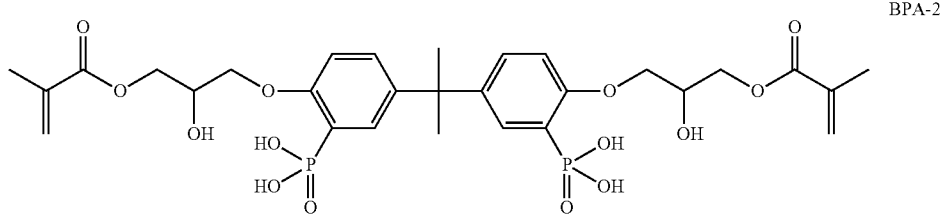

BPA-2

However, such aromatic bisphosphonic acid derivatives are characterized overall by low solubility in water, acetone, alcohol and mixtures thereof.

Therefore, it is an object of the invention to provide adhesive dental materials which are readily polymerizable, strongly acidic and soluble in polar solvents and their mixtures with water, promote good substrate adhesion to the dental hard tissue and/or dental ceramics and thus above all are suitable for the preparation of adhesives, adhesive cements and composites.

This object is achieved according to the invention by dental materials based on a polymerizable bisphosphonic acid of Formula I:

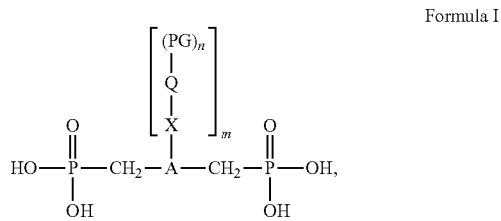

Formula I wherein

A represents an (m+2)-times substituted aliphatic $C_1$-$C_8$ radical which in each case is terminally bonded to the —$CH_2$—P(O)(OH)$_2$ groups, X in each case independently is missing or represents —O—, —S—, —CO—O—, —O—CO—, —CO—NR$^1$—, —NR$^1$—CO—, —O—CO—NR$^1$— or —NR$^1$—CO—O—, Q in each case independently is missing or represents an (n+1)-valent linear or branched aliphatic $C_1$-$C_{20}$ radical, in particular $C_1$-$C_{15}$ radical and preferably $C_1$-$C_{10}$ radical which can be interrupted by —O—, —S—, —CO—O—, —O—CO—, —CO—NR$^1$—, —NR$^1$—CO—, —O—CO—NR$^1$— or —NR$^1$—CO—O—, wherein, if Q is missing, the X adjacent to it must also be missing, PG in each case independently represents a polymerizable group selected from vinyl groups, allyl groups, $CH_2$=$CR^2$—CO—O—, $CH_2$=$CR^2$—CO—NR$^3$— and $R^4O$—CO—C(=$CH_2$)—$CH_2$—O—, $R^1$ in each case independently represents H, $CH_3$ or $C_2H_5$, $R^2$ in each case independently represents H or $CH_3$, $R^3$ and $R^4$ in each case independently represent H, a $C_1$-$C_{10}$ alkyl radical, phenyl or mesityl, n is in each case independently 1, 2 or 3 and m is 1 to 5.

The indication that a radical can be interrupted by a group, such as for example —O—, is to be understood such that the group is inserted into the carbon chain of the radical, i.e. is bordered on both sides by carbon atoms. The number of these groups is therefore at least 1 less than the number of carbon atoms and the groups cannot be terminal. According to the invention radicals which are not interrupted by the named groups are preferred.

Only compounds which are compatible with the chemical valence theory are considered in accordance with the invention.

Generally preferred are such compounds of Formula I wherein in each case independently of one another A represents an (m+2)-times substituted aliphatic $C_1$-$C_7$ radical, preferably an (m+2)-times substituted aliphatic $C_1$-$C_5$ radical, particularly preferably an (m+2)-times substituted aliphatic $C_1$-$C_3$ radical and most preferably a CH radical, X in each case independently is missing or represents —O—, —CO—O—, —O—CO—, —CO—NR$^1$— or —NR$^1$—CO— and in particular for —O—, —CO—O— or —O—CO—, Q in each case independently is missing or represents an (n+1)-valent linear or branched aliphatic $C_1$-$C_{10}$ radical, in particular $C_1$-$C_5$ radical and preferably $C_1$-$C_3$ radical, which can be interrupted by —O—, —CO—O— or —O—CO—, wherein, if Q is missing, the X adjacent to it must also be missing, PG in each case independently represents a polymerizable group selected from $CH_2$=$CR^2$—CO—O—, $CH_2$=$CR^2$—CO—NR$^3$— and $R^4O$—CO—C(=$CH_2$)—$CH_2$—O— and in particular selected from $CH_2$=$CR^2$—CO—O— and $CH_2$=$CR^2$—CO—NR$^3$—, $R^1$ in each case independently represents H, $CH_3$ or $C_2H_5$, $R^2$ in each case independently represents H or $CH_3$, $R^3$ and $R^4$ in each case independently represent H or a $C_1$-$C_7$ alkyl radical, preferably a $C_1$-$C_5$ alkyl radical, more preferably a $C_1$-$C_3$ alkyl radical and most preferably $CH_3$ or $C_2H_5$, n is in each case independently 1 or 2, and/or m is 1, 2 or 3.

Particularly preferred are compounds wherein all the variables have one of the above-defined meanings and in particular one of the preferred meanings.

According to the invention such compounds of Formula I are preferred wherein, if A represents a $C_1$ radical, (i) n+m>2 or (ii) n and m are in each case 1, X is missing and Q represents a methylene radical.

In a preferred embodiment the compound of Formula I comprises several polymerizable groups, i.e. n+m>2.

Particularly preferred in this context are such compounds of Formula I wherein

A represents an (m+2)-times substituted aliphatic $C_1$-$C_7$ radical, preferably an (m+2)-times substituted aliphatic $C_1$-$C_5$ radical, particularly preferably an (m+2)-times substituted aliphatic $C_1$-$C_3$ radical and most preferably a CH radical, X in each case independently is missing or represents —O—, —CO—O— or —O—CO—, Q in each case independently is missing or represents an (n+1)-valent linear or branched aliphatic $C_1$-$C_{10}$ radical, in particular $C_1$-$C_5$ radical and preferably $C_1$-$C_3$ radical, which can be interrupted by —O—, —CO—O— or —O—CO—, wherein, if Q is missing, the X adjacent to it must also be missing, PG in each case independently represents a polymerizable group selected from $CH_2=CR^2—CO—O—$, $CH_2=CR^2—CO—NR^3—$ and $R^4O—CO—C(=CH_2)—CH_2—$ and in particular selected from $CH_2=CR^2—CO—O—$ and $CH_2=CR^2—CO—NR^3—$, $R^2$ in each case independently represents H or $CH_3$, $R^3$ and $R^4$ in each case independently represent H, $CH_3$ or $C_2H_5$ and m is 1 and n is 2 or m is 2 or 3 and n is in each case 1.

Further particularly preferred are polymerizable bisphosphonic acids which have the Formula II:

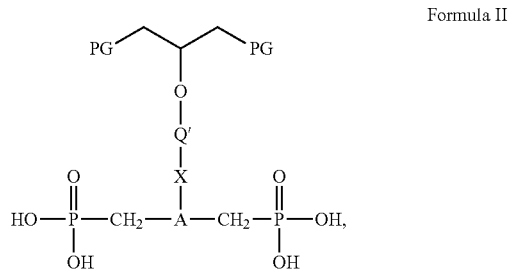

Formula II wherein

A represents a trisubstituted aliphatic $C_1$-$C_7$ radical, in particular a trisubstituted aliphatic $C_1$-$C_5$ radical, preferably a trisubstituted aliphatic $C_1$-$C_3$ radical and most preferably a CH radical, X is missing or represents —O—, Q' is missing or represents a linear or branched $C_1$-$C_7$ alkylene radical, in particular $C_1$-$C_5$ alkylene radical and preferably $C_1$-$C_3$ alkylene radical, which can be interrupted by —O—, —CO—O— or —O—CO—, PG in each case independently represents $CH_2=CR^2—CO—O—$ and $R^2$ in each case independently represents H or $CH_3$, In another preferred embodiment A in Formula I represents a (m+2)-times substituted aliphatic $C_2$-$C_8$ radical.

Particularly preferred are compounds of Formula I wherein

A represents an (m+2)-times substituted aliphatic $C_3$-$C_7$ radical,

X in each case independently is missing or represents —O—, —CO—O— or —O—CO—,

Q in each case independently is missing or represents a linear or branched $C_1$-$C_{10}$ alkylene radical, in particular $C_1$-$C_5$ alkylene radical and preferably $C_1$-$C_3$ alkylene radical, which can be interrupted by —O—, —CO—O— or —O—CO—, wherein, if Q is missing, the X adjacent to it must also be missing, PG in each case independently represents a polymerizable group selected from $CH_2=CR^2—CO—O—$, $CH_2=CR^2—CO—NR^3—$ and $R^4O—CO—C(=CH_2)—CH_2—O—$, $R^2$ in each case independently represents H or $CH_3$, $R^3$ and $R^4$ in each case independently represent H, $CH_3$ or $C_2H_5$, n is 1 and m is 1, 2 or 3.

Quite particularly preferred are polymerizable bisphosphonic acids which have the Formula III:

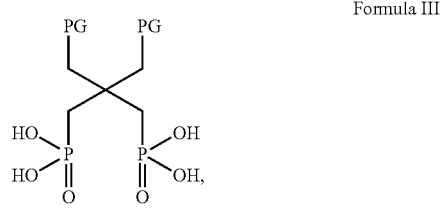

Formula III wherein

PG independently represents a polymerizable group selected from $CH_2=CR^2—CO—O—$, $CH_2=CR^2—CO—NR^3—$ and in particular $CH_2=CR^2—CO—O—$, $R^2$ independently represents H or $CH_3$ and preferably $CH_3$, $R^3$ independently represents H or preferably a $C_1$-$C_{10}$ alkyl radical, in particular a $C_1$-$C_7$ radical, preferably a $C_1$-$C_5$ radical, more preferably a $C_1$-$C_3$ radical and most preferably $CH_3$ or $C_2H_5$.

It is further preferred that the groups PG, $R^2$ or $R^3$ are in each case the same.

Particularly preferred are also polymerizable bisphosphonic acids which have the Formula IV:

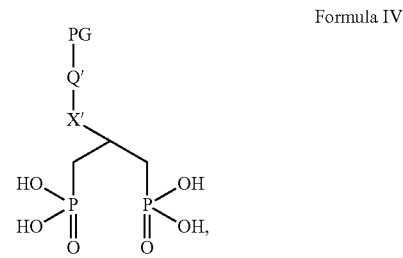

Formula IV wherein

X' in each case independently is missing or represents —O—, —S—, —CO—O—, —O—CO—, —CO—$NR^1$—, —$NR^1$—CO—, —O—CO—$NR^1$— or —$NR^1$—CO—O—, Q' in each case independently is missing or represents an (n+1)-valent linear or branched aliphatic $C_1$-$C_{10}$ radical, in particular $C_1$-$C_5$ radical, preferably $C_1$-$C_3$ radical and particularly preferably $C_1$-$C_2$ radical, which can be interrupted by —O—, —S—, —CO—O—, —O—CO—, —CO—$NR^1$—, —$NR^1$—CO—, —O—CO—$NR^1$— or —$NR^1$—CO—O—, wherein X' and Q' can only be missing simultaneously, PG represents a polymerizable group selected from $CH_2=CR^2—CO—O—$, $CH_2=CR^2—CO—NR^3—$ and $R^4O—CO—C(=CH_2)—CH_2—O—$, in particular selected from $CH_2=CR^2—CO—O—$ and $CH_2=CR^2—CO—NR^3—$ and preferably $CH_2=CR^2—CO—NR^3—$, $R^2$ represents H or $CH_3$ and preferably $CH_3$, $R^3$ represents H or preferably a $C_1$-$C_{10}$ alkyl radical, in particular a $C_1$-$C_7$ radical, preferably a $C_1$-$C_5$ radical, more preferably a $C_1$-$C_3$ radical and most preferably $CH_3$ or $C_2H_5$.

Quite particularly preferred are polymerizable bisphosphonic acids which have the Formula V:

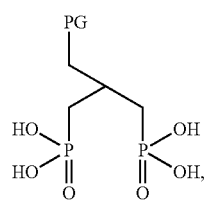

Formula V wherein
PG represents a polymerizable group selected from $CH_2=CR^2—CO—O—$, $CH_2=CR^2—CO—NR^3—$ and $R^4O—CO—C(=CH_2)—CH_2—O—$, in particular selected from $CH_2=CR^2—CO—O—$ and $CH_2=CR^2—CO—NR^3—$ and preferably $CH_2=CR^2—CO—NR^3—$,
$R^2$ represents H or $CH_3$ and preferably $CH_3$,
$R^3$ represents H or preferably a $C_1$-$C_{10}$ alkyl radical, in particular a $C_1$-$C_7$ radical, preferably a $C_1$-$C_5$ radical, more preferably a $C_1$-$C_3$ radical and most preferably $CH_3$ or $C_2H_5$.

Surprisingly it was found that the dental materials according to the invention which comprise at least one polymerizable bisphosphonic acid of Formula I exhibit a very high tendency towards radical polymerization and are simultaneously strongly acidic and readily soluble in polar solvents and their mixtures with water and after polymerization exhibit excellent adhesion to the dental hard tissue and dental ceramics.

The polymerizable bisphosphonic acids of Formula I can be prepared easily. The introduction of the phosphonate groups can thus take place for example by a Michaelis-Arbuzov reaction starting from compounds with at least two different functional groups, which comprise two phosphonizable groups Y such as e.g. halogen (cf. Group of authors, Organikum, 21$^{st}$ ed., Wiley-VCH, Weinheim etc., 2001, 246 et seq.), wherein the available further functional groups D, such as e.g. OH or $NHR^3$, are optionally to be protected by corresponding protective groups. The polymerizable groups can then be introduced into the obtained bisphosphonate by reaction with an acrylic acid derivative $CH_2=C(R^2)—CO—Z$ and the phosphonic acid groups can then be released by reaction with trimethylsilyl bromide (TMSBr) and subsequent methanolysis (cf. S. Freeman, J. Chem. Soc., Perkin Trans. 2 (1991) 263.):

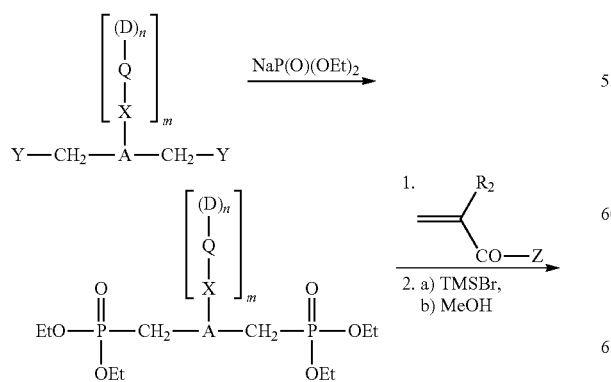

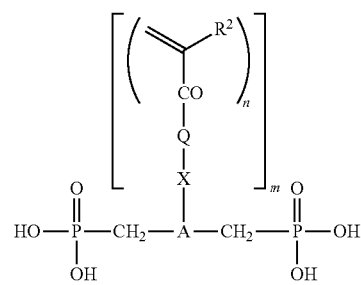

Specific Example: Starting with commercially available 2,2-(bis(bromomethyl)-1,3-propanediol (A=CH, X is missing, Q=$CH_2$, D=OH, Y=Br, m=2, n=1), the two OH groups are protected by ketalization e.g. with acetone. The two phosphonic acid groups are then introduced by reaction with sodium diethyl phosphite. The protective groups are cleaved off from the formed bisphosphonate by methanolysis in the presence of a strongly acidic ion-exchange resin as catalyst, the polymerizable methacrylate groups (PG=$CH_2=C(CH_3)—CO—O—$) are introduced by acylation with methacrylic acid chloride ($R^2$=$CH_3$, Z=Cl) and finally the phosphonic acid groups are released:

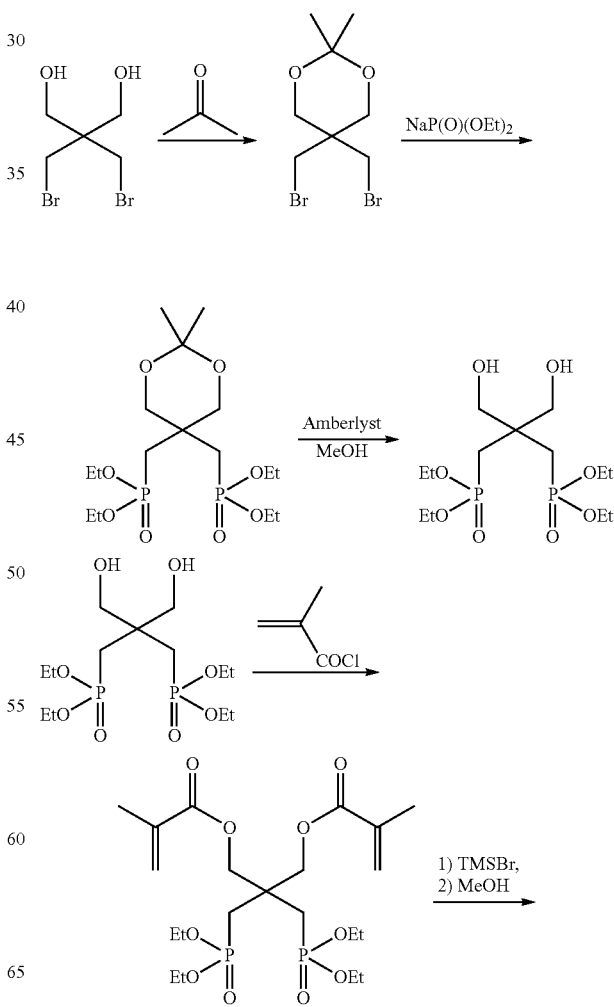

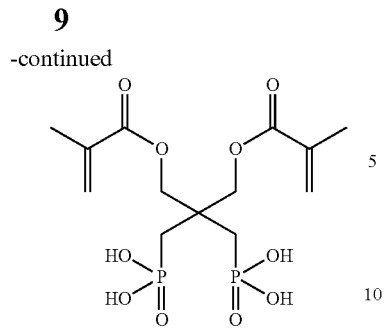

Suitable starting materials for the synthesis of polymerizable bisphosphonic acids of Formula I are, in addition to pentaerythritol, also other commercially polyhydric alcohols such as e.g. glycerol, trimethylolethane, 1,2,4-butanetriol or trimethylolpropane.

Another general option for the synthesis of polymerizable bisphosphonic acids of Formula I is to separately synthesize a bisphosphonate component and a polymerizable component and then to join both components together. A bisphosphonate component with A=CH can thus be prepared by Michaelis-Arbuzov reaction of epibromohydrin with triethyl phosphite and subsequent epoxide ring-opening with triethyl phosphite in the presence of zinc chloride and reacted with an equimolar amount of a diisocyanate OCN-D-NCO to give an isocyanate-terminated bisphosphonate component. This synthesis component is then reacted with a commercially available OH-terminated compound $(PG)_n$-E-OH which comprises n polymerizable groups. After liberation of the phosphonic acid groups, polymerizable bisphosphonic acids with X=—O—CO—NH—, Q=-E-NH—CO—O—$Y^2$ and m=1 are obtained:

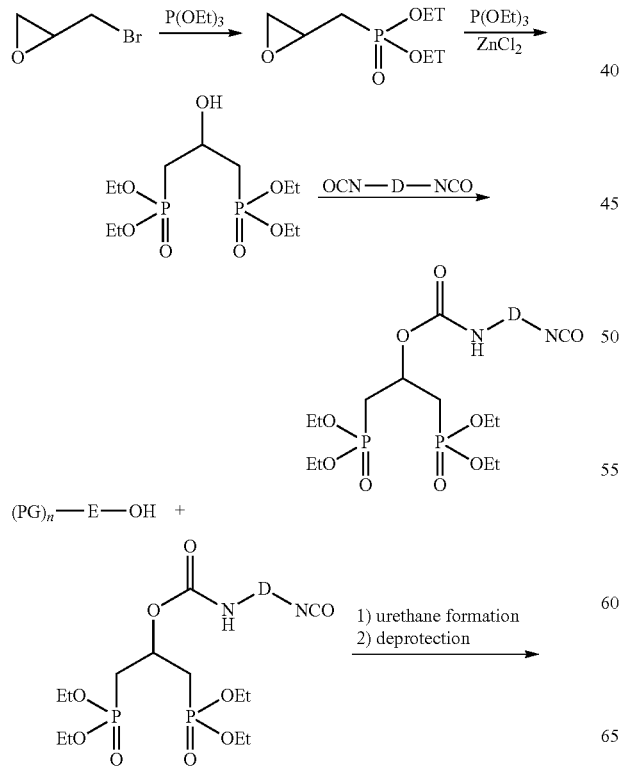

Specific Example: Reaction of the OH-terminated $C_3$ bisphosphonate component with hexamethylene-1,6-diisocyanate (HMDI), reaction with glycerol-1,3-dimethacrylate (GDMA) and release of the phosphonic acid groups:

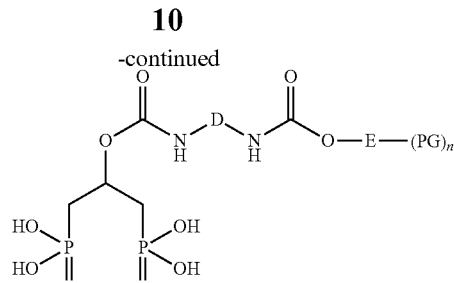

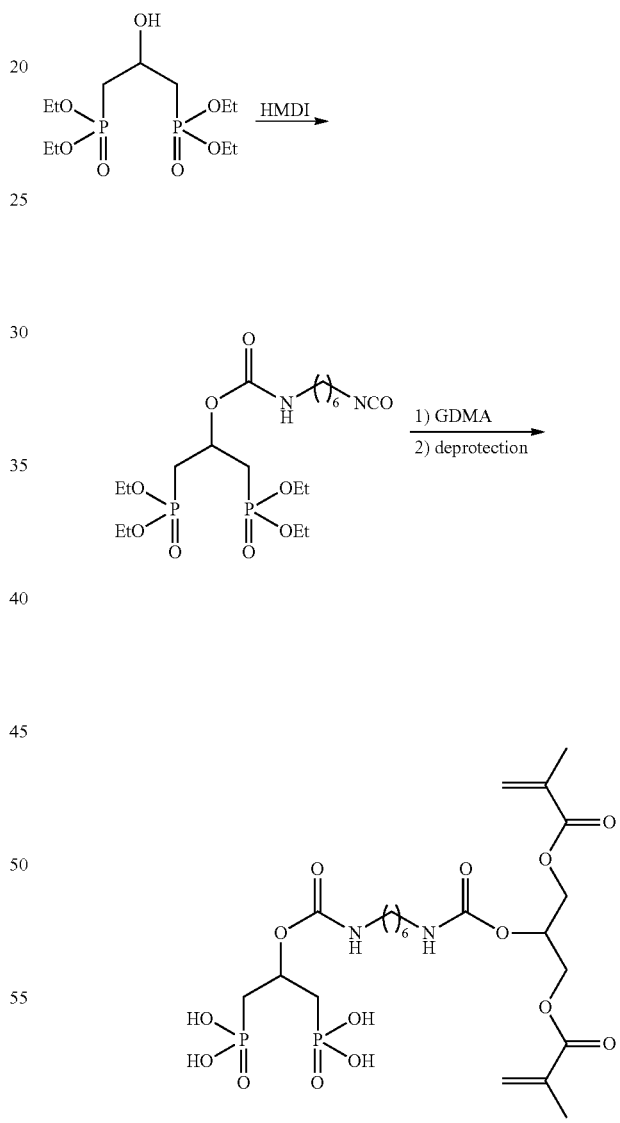

Further OH-terminated compounds, suitable for the synthesis of polymerizable bisphosphonic acids of Formula I, which carry n polymerizable groups, are for example trimethylolpropane di(meth)acrylate, pentaerythritol tri(meth)acrylate, dipentaerythritol penta(meth)acrylate and 1,3-bis(meth)acrylamido-2-hydroxypropane.

Examples of polymerizable bisphosphonic acids of Formula I according to the invention are:
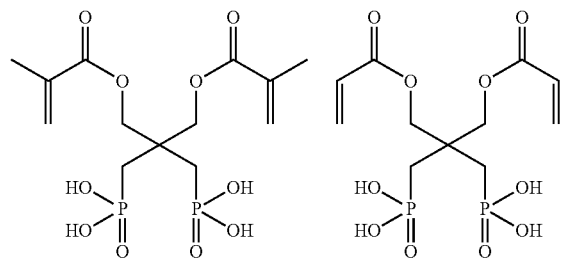
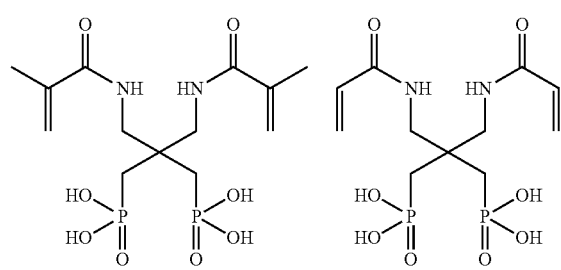
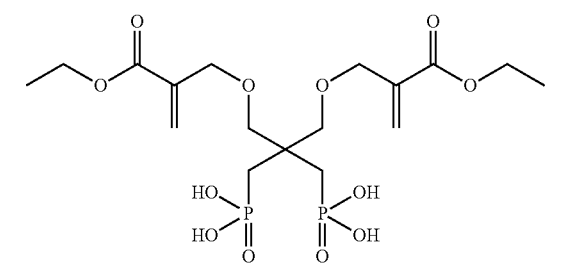
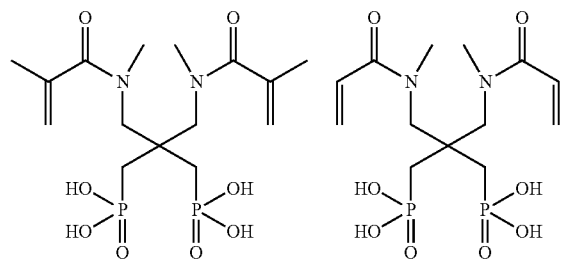
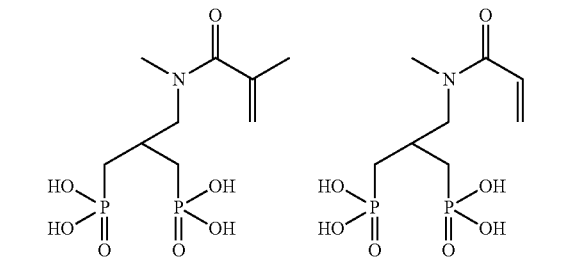
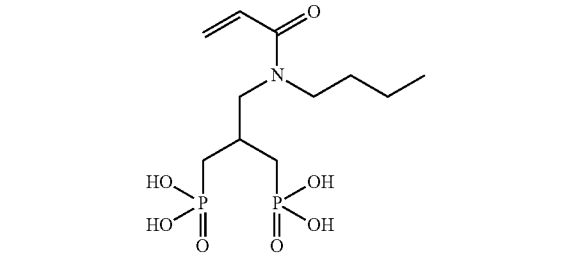
-continued
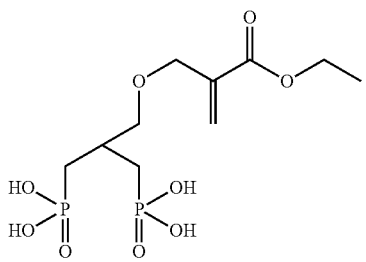
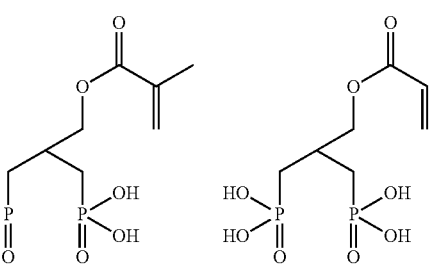
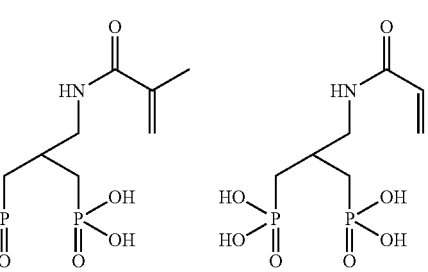
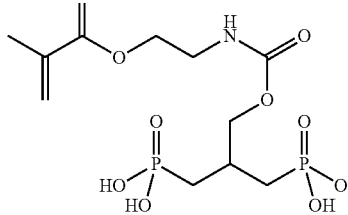
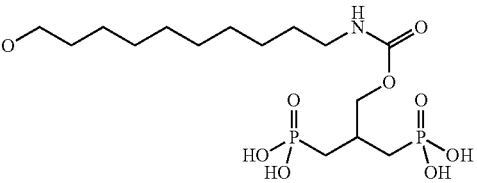
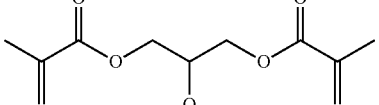
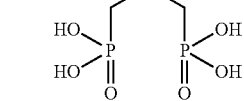

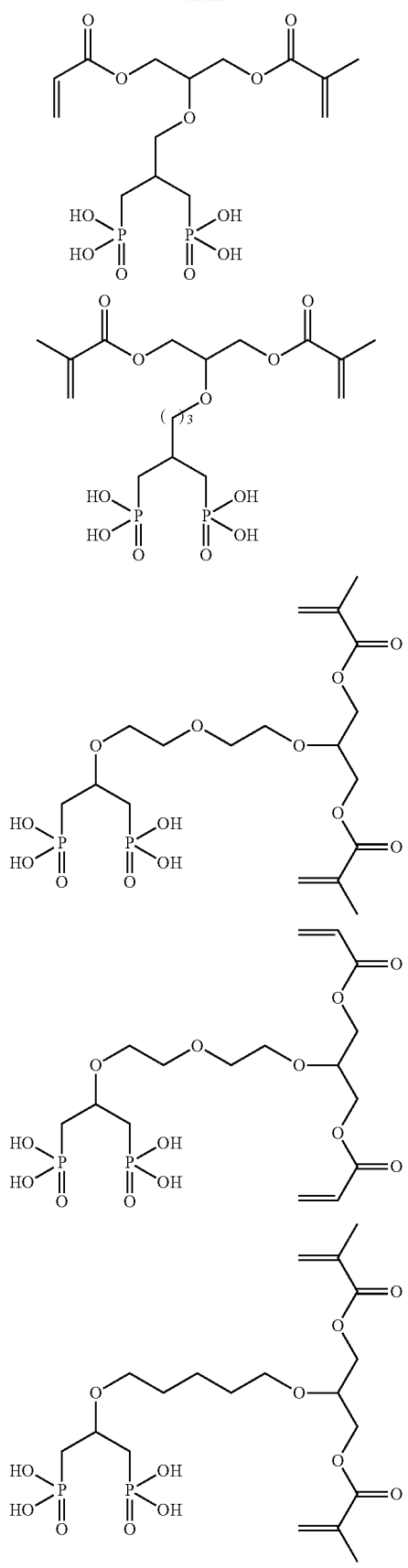
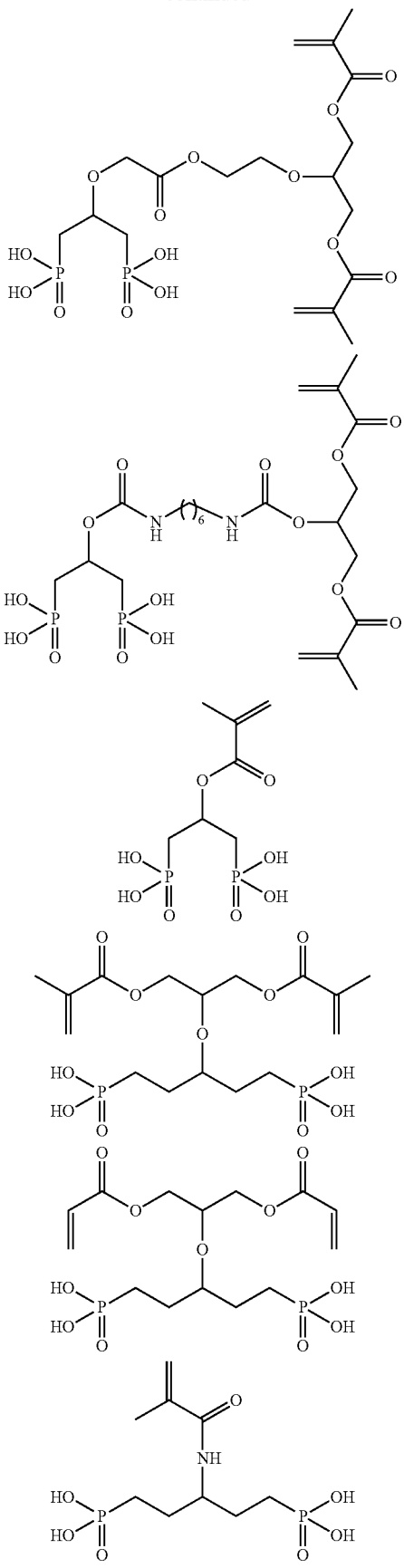

-continued

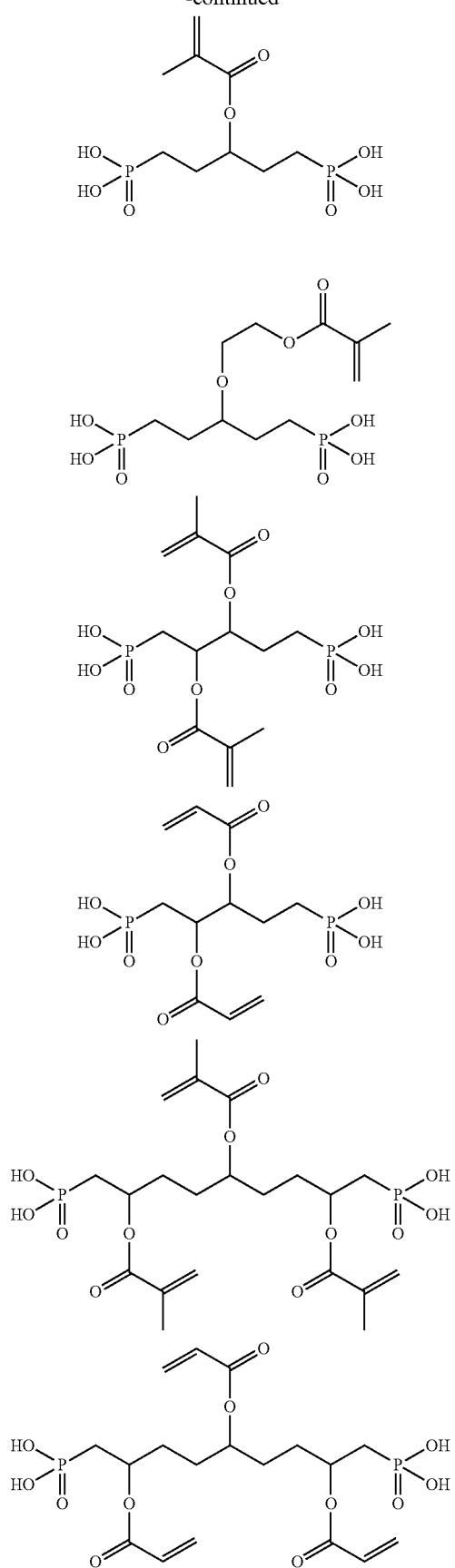

-continued

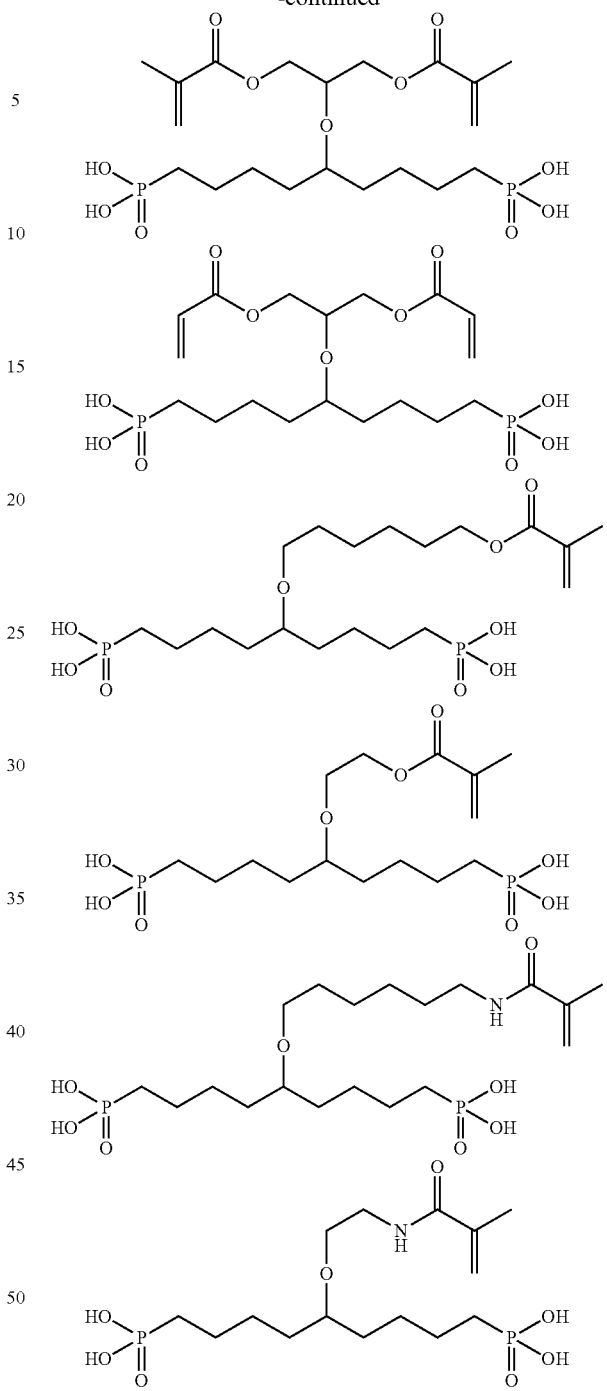

The dental materials according to the invention preferably comprise, in addition to the polymerizable bisphosphonic acid of Formula I, one or more additional radically polymerizable monomers (co-monomers), in particular mono- or polyfunctional (meth)acrylic acid derivatives. By monofunctional (meth)acrylic acid derivatives are meant compounds with one, by polyfunctional (meth)acrylic acid derivatives are meant compounds with two or more, preferably 2 to 4 (meth)acrylic acid groups. Polyfunctional monomers have a cross-linking effect.

Preferred mono- or polyfunctional (meth)acrylic acid derivatives according to the invention are methyl, ethyl, hydroxyethyl, butyl, benzyl, tetrahydrofurfuryl or isobornyl (meth)acrylate, bisphenol-A-di(meth)acrylate, bis-GMA (an addition product of methacrylic acid and bisphenol-A-diglycidyl ether), UDMA (an addition product of 2-hydroxyethyl methacrylate (HEMA) and 2,2,4-trimethylhexamethylene diisocyanate), di-, tri- or tetraethylene glycol di(meth)acrylate, trimethylolpropane tri(meth)acrylate, pentaerythritol tetra(meth)acrylate, glycerol di(meth)acrylate, 1,4-butanediol di(meth)acrylate, 1,10-decanediol di(meth)acrylate and 1,12-dodecanediol di(meth)acrylate.

Particularly preferred mono- or polyfunctional (meth) acrylic acid derivatives are N-mono- or -disubstituted acrylamides, such as N-ethylacrylamide, N,N-dimethacrylamide, N-(2-hydroxyethyl)acrylamide or N-methyl-N-(2-hydroxyethyl)acrylamide, N-monosubstituted methacrylamides such as N-ethylmethacrylamide or N-(2-hydroxyethyl)methacrylamide as well as N-vinylpyrrolidone and allyl ethers. These monomers are characterized by high stability against hydrolysis and are particularly suitable as diluting monomers because of their relatively low viscosity.

Preferred polyfunctional (meth)acrylic acid derivatives with high stability against hydrolysis are cross-linking pyrrolidones, such as 1,6-bis(3-vinyl-2-pyrrolidonyl)-hexane, bisacrylamides such as methylene or ethylene bisacrylamide and bis(meth)acrylamides such as N,N'-diethyl-1,3-bis(acrylamido)-propane, 1,3-bis(methacrylamido)-propane, 1,4-bis(acrylamido)-butane or 1,4-bis(acryloyl)-piperazine, which can be synthesized by reaction of the corresponding diamines with (meth)acrylic acid chloride.

It is preferred to use mixtures of the above monomers.

In addition to the polymerizable bisphosphonic acid of Formula I and optionally the above-named co-monomers, the dental materials according to the invention can preferably also comprise additional radically polymerizable, acid group-containing monomers (adhesive monomers). Preferred acid groups are carboxylic acid groups, phosphonic acid groups, phosphoric acid groups and sulphonic acid groups.

Preferred monomers with polymerizable carboxylic acids are maleic acid, acrylic acid, methacrylic acid, 2-(hydroxymethyl)-acrylic acid, 4-(meth)acryloyloxyethyltrimellitic anhydride, 10-methacryloyloxydecylmalonic acid, N-(2-hydroxy-3-methacryloyloxypropyl)-N-phenylglycine and 4-vinylbenzoic acid.

Preferred monomers with polymerizable phosphonic acid groups are vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid, 2-[4-(dihydroxyphosphoryl)-2-oxa-butyl]-acrylic acid ethyl- and -2,4,6-trimethylphenyl ester.

Preferred monomers with polymerizable phosphoric acid groups are 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritol-pentamethacryloyloxyphosphate, 10-methacryloyloxydecyl-dihydrogen phosphate, phosphoric acid mono-(1-acryloyl-piperidine-4-yl)-ester, 6-(methacrylamido)hexyl dihydrogen phosphate and 1,3-bis-(N-acryloyl-N-propyl-amino)-propan-2-yl-dihydrogen phosphate.

Preferred monomers with polymerizable sulphonic acid groups are vinylsulphonic acid, 4-vinylphenylsulphonic acid and 3-(methacrylamido)propylsulphonic acid.

Moreover, the dental materials according to the invention preferably also comprise an initiator for radical polymerization.

To initiate radical photopolymerization, benzophenone, benzoin and derivatives thereof or α-diketones or derivatives thereof, such as 9,10-phenanthrenequinone, 1-phenyl-propane-1,2-dione, diacetyl or 4,4'-dichlorobenzil are preferably used. It is particularly preferred to use camphorquinone and 2,2-dimethoxy-2-phenyl-acetophenone, and quite particularly preferably α-diketones in combination with amines such as 4-(dimethylamino)-benzoate, N,N-dimethylaminoethyl methacrylate, N,N-dimethyl-sym.-xylidine or triethanolamine as reducing agents. Norrish type I photoinitiators, in particular acyl- or bisacylphosphine oxides, monoacyltrialkyl- or diacyldialkylgermanium compounds, such as benzoyltrimethylgermanium, dibenzoyldiethylgermanium or bis (4-methoxybenzoyl)diethylgermanium are also particularly suitable. Mixtures of the different photoinitiators can also be used, such as for example dibenzoyldiethylgermanium combined with camphorquinone and 4-dimethylaminobenzoic acid ethyl ester.

Preferably, redox-initiator combinations, such as for example combinations of benzoyl peroxide with N,N-dimethyl-sym.-xylidine or N,N-dimethyl-p-toluidine, are used as initiators for a polymerization carried out at room temperature. In addition, redox systems consisting of peroxides and reducing agents such as e.g. ascorbic acid, barbiturates or sulphinic acids are also particularly suitable.

The compositions used according to the invention further preferably also comprise organic or inorganic filler particles to improve the mechanical properties or to adjust the viscosity. Preferred inorganic particulate fillers are amorphous spherical materials based on oxides, such as $ZrO_2$ and $TiO_2$ or mixed oxides of $SiO_2$, $ZrO_2$ and/or $TiO_2$ having an average particle size of 0.005 to 2.0 µm, preferably 0.1 to 1 µm, nanoparticulate or microfine fillers such as pyrogenic silica or precipitated silica having an average particle size of 5 to 200 nm, preferably 10 to 100 nm, minifillers such as quartz, glass ceramic or glass powder having an average particle size of from 0.01 to 10 µm, preferably 0.1 to 1 µm, as well as X-ray opaque fillers such as ytterbium trifluoride or nanoparticulate tantalum(V) oxide or barium sulphate having an average particle size of 10 nm to 1000 nm, preferably 100 to 300 nm.

The compositions used according to the invention can also comprise further additives, particularly solvents such as water or ethanol or corresponding solvent mixtures as well as for example stabilizers, flavourings, dyes, microbiocidal active ingredients, fluoride-ion releasing additives, optical brighteners, plasticizers or UV absorbers.

Particularly preferred are dental materials on the basis of a polymerizable bisphosphonic acid of Formula I, and in particular on the basis of a polymerizable bisphosphonic acid of Formula II, III, IV or V, which comprise the following constituents:
a) 0.1 to 50 wt.-%, in particular 1 to 40 wt.-%, preferably 2 to 30 wt.-% and particularly preferably 5 to 20 wt.-% polymerizable bisphosphonic acid of Formula I,
b) 0.01 to 10 wt.-%, preferably 0.1 to 3 wt.-% and particularly preferably 0.2 to 2 wt.-% initiator,
c) 0 to 80 wt.-%, preferably 1 to 60 wt.-% and particularly preferably 5 to 50 wt.-% co-monomer,
d) 0 to 30 wt.-%, preferably 0.5 to 15 wt.-% and particularly preferably 1 to 5 wt.-% adhesive monomer,
e) 0 to 80 wt.-% filler and
f) 0 to 70 wt.-%, preferably 0 to 60 wt.-% and particularly preferably 0 to 50 wt.-% solvent.

The preferred filler content depends on the desired use. Adhesives preferably comprise 0 to 20 wt.-% and cements and composites preferably comprise 20 to 80 wt.-% filler.

The same applies to the solvent content. Adhesives preferably comprise 0 to 60 wt.-% and particularly preferably 1 to 50 wt.-% solvent. Dental materials which comprise water as solvent are preferred. Dental materials which comprise 0 to 20 wt.-% and in particular 1 to 10 wt.-% water are particularly preferred.

The invention is explained in more detail below with reference to examples.

EXAMPLES

Example 1

Synthesis of 3-(methacryloyloxy)-2,2-(di[(dihydroxyphosphoryl)-methyl])propyl methacrylate (DMPBPA)

$1^{st}$ step: 5,5-di[(diethoxyphosphoryl)methyl]-2,2-dimethyl-1,3-dioxane

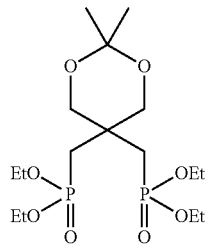 [SMILES: CCOP(=O)(CC1(CP(=O)(OCC)OCC)COC(C)(C)OC1)OCC]

Sodium diethyl phosphite (63.6 g, 400 mmol, 6.0 eq.) was added to a solution of 5,5-di(bromomethyl)-2,2-dimethyl-1,3-dioxane (20.0 g, 66 mmol) in an anhydrous mixture of THF/DMF (9:1, 600 ml). The reaction mixture was stirred for 15 h at 68° C. and subsequently mixed with a saturated aqueous solution of ammonium chloride (20.0 ml) and the volatile constituents were removed in vacuo. The residue was diluted with deionized water (200 ml) and the solution formed was extracted with methylene chloride (3×200 ml). The combined organic phases were dried with anhydrous sodium sulphate and the solvent was then removed under reduced pressure. The obtained crude product was purified by flash column chromatography (eluent: ethyl acetate/methanol 9:1). 19.6 g (71% yield) of the product was obtained as a colorless oil.

$^1$H-NMR (400 MHz, CDCl$_3$): δ=1.32 (t, $^3J_{HH}$=7.0 Hz, 12H, POCH$_2$C$\underline{H}_3$); 1.41 (s, 6H, CH$_3$); 2.29 (d, $^2J_{HP}$=19.2 Hz, 4H, CH$_2$P); 3.85 (s, 4H, CCH$_2$O); 4.05-4.15 (m, 8H, PO C$\underline{H}_2$CH$_3$), $^{31}$P NMR (162 MHz, CDCl$_3$): δ=29.0.

$^{13}$C-NMR (101 MHz, CDCl$_3$): δ=16.4 (d, $^3J_{CP}$=6.5 Hz, POC$\underline{H}_2$CH$_3$); 23.8 (CH$_3$); 28.3 (dd, $^1J_{CP}$=138.3 Hz, $^3J_{CP}$=4.0 Hz, CH$_2$P); 33.7 (t, $^2J_{CP}$=3.0 Hz, $\underline{C}$CH$_2$P); 61.6 (d, $^2J_{CP}$=6.7 Hz, PO$\underline{C}$H$_2$CH$_3$); 68.0 (t, $^3J_{CP}$=10.7 Hz, O$\underline{C}$H$_2$CCH$_2$P); 98.3 ($\underline{C}$CH$_3$).

HRMS (m/z): calc. for C$_{16}$H$_{35}$O$_8$P$_2$: 417.18: found: 417.18 [M+H]$^+$.

$2^{nd}$ step: 3-(methacryloyloxy)-2,2-(di[(diethoxyphosphoryl)methyl])-propyl methacrylate

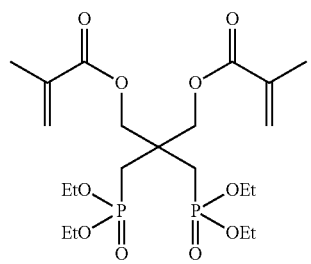 [SMILES: C=C(C)C(=O)OCC(COC(=O)C(=C)C)(CP(=O)(OCC)OCC)CP(=O)(OCC)OCC]

1.95 g of the ion-exchange resin Amberlyst H-15 was added to a solution of the bisphosphonate from the $1^{st}$ step (19.55 g, 47 mmol) in anhydrous methanol (600 ml) and the mixture was stirred for 11 h at 25° C. After filtration of the solution, the solvent was removed in vacuo. 17.5 g of an oily crude product was obtained, which was added to a mixture of dry methylene chloride (120 ml), triethylamine (16.9 ml, 12 mmol) and 4-(N,N-dimethylamino)-pyridine (489 mg, 4.0 mmol). Methacrylic acid anhydride (18.1 ml, 12 mmol) was then slowly added dropwise at room temperature and the reaction mixture was stirred for 15 h. Deionized water (60 ml) was added for work-up, the phases were separated and the aqueous phase was extracted with methylene chloride (3×60 ml). The combined organic phases were dried with anhydrous sodium sulphate. After removal of the solvent under reduced pressure, the obtained crude product was purified by flash column chromatography (eluent: ethyl acetate/methanol 97:3). 10.3 g (43% yield) of the product was obtained as yellow solid (mp=43-45° C.).

$^1$H-NMR (400 MHz, CDCl$_3$): δ=1.28 (t, $^3J_{HH}$=7.0 Hz, 12H, POCH$_2$C$\underline{H}_3$); 1.93 (s, 6H, CH$_2$=CC$\underline{H}_3$); 2.34 (d, $^2J_{HP}$=19.9 Hz, 4H, CH$_2$P); 4.03-4.14 (m, 8H, POC$\underline{H}_2$CH$_3$); 4.22 (s, 4H, CCH$_2$O); 5.55-5.58 (m, 2H, C=CH$_2$); 6.08-6.11 (m, 2H, C=CH$_2$).

$^{31}$P-NMR (162 MHz, CDCl$_3$): δ=28.0.

$^{13}$C-NMR (101 MHz, CDCl$_3$): δ=16.3 (d, $^3J_{CP}$=6.2 Hz, POC$\underline{H}_2$CH$_3$); 18.3 (CH$_2$=CC$\underline{H}_3$); 27.8 (dd, $^1J_{CP}$=139.5 Hz, $^3J_{CP}$=4.3 Hz, CH$_2$P); 38.3 (t, $^2J_{CP}$=2.7 Hz, $\underline{C}$CH$_2$P); 61.7 (d, $^2J_{CP}$=7.0 Hz, PO$\underline{C}$H$_2$CH$_3$); 66.5 (t, $^3J_{CP}$=12.8 Hz, O$\underline{C}$H$_2$CCH$_2$P); 126.0 (C=$\underline{C}$H$_2$); 136.0 ($\underline{C}$=CH$_2$); 166.6 ($\underline{C}$=O).

HRMS (m/z): calc. for C$_{21}$H$_{39}$O$_{10}$P$_2$: 513.20; found: 513.20 [M+H]$^+$.

$3^{rd}$ step: 3-(methacryloyloxy)-2,2-(di[(dihydroxyphosphoryl)methyl])-propyl methacrylate (DMPBPA)

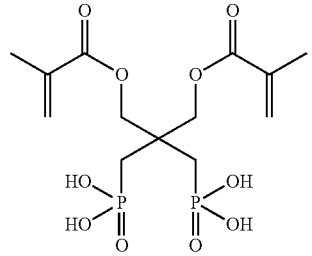 [SMILES: C=C(C)C(=O)OCC(COC(=O)C(=C)C)(CP(=O)(O)O)CP(=O)(O)O]

Trimethylsilyl bromide (14.9 ml, 112.5 mmol, 6 eq.) was added dropwise to a solution of the bisphosphonate from the $2^{nd}$ step (9.6 g, 18.75 mmol) in methylene chloride (80 ml) and the reaction mixture was stirred for 5 h at 30° C. The mixture was then concentrated under reduced pressure, mixed with methanol (80 ml) and stirred for 30 min at room temperature. After the addition of 3,5-di-tert-butyl-4-hydroxy toluene (BHT, 200 ppm) and galvinoxyl radicals (20 ppm), volatile constituents were removed in a weak vacuum and the product was dried in a fine vacuum (0.07 mbar) to a constant weight. 7.1 g (95% yield) of the product was obtained as a white solid (mp>142° C.) with very good solubility in water, ethanol, acetone and THF.

$^1$H-NMR (400 MHz, MeOH-d$_4$): δ=1.95 (s, 6H, CH$_2$=C C$\underline{H}_3$); 2.26 (d, $^2J_{HP}$=19.6 Hz, 4H, CH$_2$P); 4.36 (s, 4H, CCH$_2$O); 5.62-5.65 (m, 2H, C=CH$_2$); 6.12 (s, 2H, C=CH$_2$).

$^{31}$P-NMR (162 MHz, MeOH-d$_4$): δ=24.8.

$^{13}$C-NMR (101 MHz, MeOH-d$_4$): δ=18.5 (CH$_2$=CC$\underline{H}_3$); 31.4 (dd, $^1J_{CP}$=137.1 Hz, $^3J_{CP}$=5.9 Hz, CH$_2$P); 39.4 (t, $^2J_{CP}$=3.0 Hz, $\underline{C}$CH$_2$P); 68.1 (t, $^3J_{CP}$=10.1 Hz, O$\underline{C}$H$_2$CCH$_2$P); 126.5 (C=$\underline{C}$H$_2$); 137.5 ($\underline{C}$=CH$_2$); 168.2 (C=O).

HRMS (m/z): calc. for C$_{13}$H$_{21}$O$_{10}$P$_2$: 399.06; found: 399.06 [M−H]$^-$.

Example 2

Radical Solution Polymerization of the Bisphosphonic Acid Dimethacrylate DMPBPA

Homogeneous mixtures of 2.5 mmol each of the bisphosphonic acid dimethacrylate from Example 1 (DMPBPA) or glycerol dimethacrylate (GDMA; comparison) and 1 mol-% (relative to the monomer) 2,2'-azobis-(2-methylpropionamidine)-dihydrochloride in 2.5 ml of a water/ethanol mixture (1:2 v/v) were prepared in Schlenk vessels and degassed by passing argon therethrough. The polymerization batches were then heated to 65° C. in a thermostat. The time after which a three-dimensional, firm gel formed was determined as the gelling time.

| Cross-linker | Gelling time (min) |
| --- | --- |
| DMPBPA | 1.5 |
| GDMA (comparison) | 1.8 |

The results show that the bisphosphonic acid dimethacrylate DMPBPA shows a cross-linking reactivity comparable with that of GDMA.

Example 3

Radical Photopolymerization of the Bisphosphonic Acid Dimethacrylate DMPBPA

Photopolymerization experiments were carried out by means of a Perkin Elmer differential scanning calorimeter DSC-7 using 0.4 wt.-% bis-(4-methoxybenzoyl)diethylgermanium as photo-initiator. In each case 0.8 mg of the examined monomer mixture based on 2-hydroxyethyl methacrylate (HEMA) and GDMA or DMPBPA was placed in open aluminium pans. The DSC chamber was rinsed with nitrogen for 5 min prior to the photopolymerization. The samples were irradiated for 2 min at 37° C. with a bluephase LED lamp (Ivoclar Vivadent AG) with the incident light intensity being 40 mW·cm$^2$ and each experiment being repeated three times. The polymerization rate $R_P$ was calculated according to the following formula: $R_P=Q/(m·\Delta H_{0P})$, wherein Q represents the heat flow per second, m represents the mass of the monomer sample and $\Delta H_{0P}$ represents the polymerization enthalpy of dimethacrylates (109.7 kJ·mol$^{-1}$). The time $t_{max}$ to reach the maximum polymerization rate $R_{p,max}$ was determined from the DSC curve.

| Monomer mixture (mol/mol) | $t_{max}$ (s) | $R_{p,max}$ (s$^{-1}$) |
| --- | --- | --- |
| HEMA/GDMA (7:3; comparison) | 9.0 ± 0.2 | 0.051 ± 0.004 |
| HEMA/DMPBPA/GDMA (5:2:3) | 2.0 ± 0.1 | 0.096 ± 0.005 |

The results demonstrate the very high photopolymerization reactivity of the DMPBPA-containing mixture compared with the pure HEMA/GDMA mixture.

Example 4

Preparation of a Light-curing Adhesive Based on DMPBPA from Example 1

To examine the dentine adhesion on bovine tooth dentine, an adhesive having the composition given in Table 1 were prepared:

TABLE 1

| Composition of the adhesive (values in mass-%) | |
| --- | --- |
| Component | Adhesive A |
| DMPBPA | 10.9 |
| Glycerol dimethacrylate | 9.9 |
| UDMA[1] | 9.9 |
| Bis-GMA[2] | 32.7 |
| 2-hydroxyethyl methacrylate | 14.9 |
| Photoinitiator[3] | 1.7 |
| Ethanol (abs.) | 20.0 |

[1]UDMA (addition product of 2-hydroxyethyl methacrylate and 2,2,4-trimethyl hexamethylene diisocyanate),
[2]Bis-GMA (addition product of methacrylic acid and bisphenol-A diglycidyl ether),
[3]mixture of camphorquinone (0.3%), 4-dimethyl-benzoic acid ethyl ester (0.4%) and the acylphosphine oxide Lucerin TPO (1.0%)

Bovine teeth were embedded in plastic cylinders in such a way that the dentine and the plastic were on one level. After 15 s etching with 37% phosphoric acid, the teeth were rinsed thoroughly with water. A layer of adhesive of the above composition was then brushed on with a microbrush, briefly blown with an air blower to remove the solvent and exposed to light for 40 s with a halogen lamp (Astralis 7, Ivoclar Vivadent AG). A composite cylinder of Tetric® Ceram (Ivoclar Vivadent) was polymerized onto the adhesive layer in two layers of 1-2 mm each. The testpiece was then stored in water for 24 h at 37° C. and the adhesive shear strength was determined according to the ISO guideline "ISO 1994-ISO TR 11405: Dental Materials Guidance on Testing of Adhesion to Tooth Structure" at 31.7 MPa.

Example 5

Synthesis of 2-methacryloyloxy-1,3-propylene-bisphosphonic acid (MPPA)

1$^{st}$ step: 2-hydroxy-1,3-propylene-bisphosphonic acid tetraethyl ester

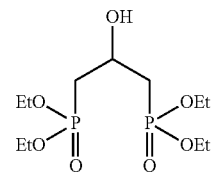 [SMILES: CCOP(=O)(CC(O)CP(=O)(OCC)OCC)OCC]

2,3-Epoxypropyl phosphonic acid diethylester was prepared according to the description in A. M. M. Phillips et al., Phosphorus, Sulfur, Silicon, Relat. Elem. 71 (1992) 165-174. The thus-obtained 2,3-epoxypropyl phosphonic acid diethylester (11.35 g, 58 mmol) was added dropwise to a mixture of triethyl phosphite (50.2 ml, 29 mmol, 5.0 eq.) and zinc chloride (8.37 g, 61 mmol, 1.05 eq.) and the reaction mixture was subsequently stirred for 15 h at room temperature. Then ethyl acetate (250 ml) was added to the reaction solution and the solution was washed with a saturated aqueous solution of ammonium chloride (2×125 ml). The combined aqueous phases were extracted with ethyl acetate (2×125 ml). The combined organic phases were dried with anhydrous sodium sulphate and then concentrated under reduced pressure. Then the excess triethyl phosphite was removed in a water-jet vacuum and the residue was dried in a fine vacuum (0.08 mbar) at 100° C. to a constant weight. The obtained crude product was purified by column chromatography (eluent: ethyl acetate/methanol 9:1). 8.2 g (42% yield) of the product was obtained as a light yellow oil.

$^1$H NMR (400 MHz, CDCl$_3$): δ=1.31, 1.32 (2t, $^3J_{HH}$=7.0 Hz, 12H, POCH$_2$CH$_3$); 2.00-2.22 (m, 4H, CH$_2$P); 4.04-4.19 (m, 9H, POCH$_2$CH$_3$ and OH); 4.30-4.45 (m, 1H, CHOH).

$^{31}$P NMR (162 MHz, CDCl$_3$): δ=28.4.

$^{13}$C NMR (101 MHz, CDCl$_3$): δ=16.3-16.5 (m, POCH$_2$CH$_3$); 34.2 (dd, $^1J_{CP}$=139.3 Hz, $^3J_{CP}$=13.2 Hz, CH$_2$P); 61.8-62.2 (m, POCH$_2$CH$_3$); 62.4 (t, $^2J_{CP}$=2.9 Hz, CHOH).

2$^{nd}$ step:
2-methacryloyloxy-1,3-propylene-bisphosphonic acid tetraethyl ester

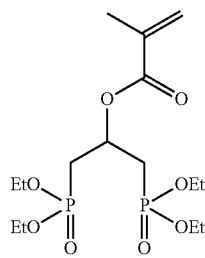 [SMILES: C=C(C)C(=O)OC(CP(=O)(OCC)OCC)CP(=O)(OCC)OCC]

Methacrylic acid anhydride (4.0 ml, 27 mmol, 1.5 eq.) was added dropwise to a mixture of the bisphosphonate from the 1$^{st}$ step (5.97 g, 18.0 mmol) with triethylamine (3.76 ml, 27 mmol, 1.5 eq.), 4-dimethylaminopyridine (176 mg, 1.4 mmol, 8 mol %) and anhydrous dichloromethane (50 ml) and the solution was heated for 40 h under reflux. Deionized water (25 ml) was added for work-up, the phases were separated and the aqueous phase was extracted with dichloromethane (2×25 ml). The combined organic phases were dried with anhydrous sodium sulphate. After removal of the solvent under reduced pressure the obtained crude product was purified by column chromatography (eluent: ethyl acetate/methanol 9:1). 6.1 g (85% yield) of the product was obtained as a colorless oil.

$^1$H NMR (400 MHz, CDCl$_3$): δ=1.29, 1.31 (2t, $^3J_{HH}$=7.1 Hz, 12H, POCH$_2$CH$_3$); 1.94 (s, 3H, CH$_3$); 2.26-2.49 (m, 4H, CH$_2$P); 4.03-4.16 (m, 8H, POCH$_2$CH$_3$); 5.33-5.46 (m, 1H, CHO); 5.58-5.62 (m, 1H, CH$_2$=C); 6.18 (ls, 1H, CH$_2$=C).

$^{31}$P NMR (162 MHz, CDCl$_3$): δ=25.7.

$^{13}$C NMR (101 MHz, CDCl$_3$): δ=16.3 (d, $^3J_{CP}$=6.4 Hz, POCH$_2$CH$_3$); 16.4 (d, $^3J_{CP}$=6.4 Hz, POCH$_2$CH$_3$); 18.2 (CH$_3$); 31.1 (dd, $^1J_{CP}$=139.2 Hz, $^3J_{CP}$=8.1 Hz, CH$_2$P); 61.8 (d, $^2J_{CP}$=6.6 Hz, POCH$_2$CH$_3$); 61.9 (d, $^2J_{CP}$=6.6 Hz, POCH$_2$CH$_3$); 65.7 (t, $^2J_{CP}$=2.2 Hz, CHO); 126.3 (s, CH$_2$=C); 136.0 (s, CH$_2$=C); 166.2 (s, C=O).

3$^{rd}$ step:
2-methacryloyloxy-1,3-propylene-bisphosphonic acid (MPPA)

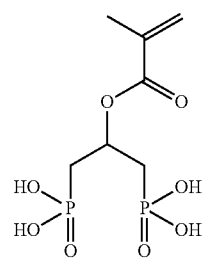

Trimethylsilyl bromide (2.97 ml, 22.5 mmol, 6.0 eq.) was added dropwise to a solution of the bisphosphonate from the 2$^{nd}$ step (1.5 g, 3.75 mmol) in anhydrous dichloromethane (15 ml) and the reaction mixture was stirred for 5 h at 30° C. Then methanol (25 ml) was added and the mixture was stirred for 30 min at room temperature. After the addition of 3,5-di-tert-butyl-4-hydroxytoluene (BHT, 200 ppm) and galvinoxyl radicals (20 ppm) the volatile constituents were removed in a weak vacuum and the residue was dried to a constant weight in a fine vacuum (0.07 mbar). 1.05 g (97% yield) of the product was obtained as a white solid.

$^1$H-NMR (400 MHz, D$_2$O): δ=1.77 (s, 3H, CH$_3$); 2.12-2.30 (m, 4H, CH$_2$P); 5.27-5.41 (m, 1H, CHO); 5.54-5.59 (m, 1H, CH$_2$=C); 6.00 (ls, 1H, CH$_2$=C).

$^{31}$P NMR (162 MHz, D$_2$O): δ=23.9.

$^{13}$C NMR (101 MHz, D$_2$O): δ=17.2 (CH$_3$); 32.3 (dd, $^1J_{CP}$=135.1 Hz, $^3J_{CP}$=10.8 Hz, CH$_2$P); 65.7 (t, $^2J_{CP}$=3.7 Hz, CHO); 127.0 (s, CH$_2$=C); 135.7 (s, CH$_2$=C); 168.1 (s, C=O).

HRMS (m/z): calc. for: C$_7$H$_{15}$O$_8$P$_2$, 289.0242; found: 289.0239 [M+H]$^+$.

Example 6

Preparation of a Light-curing Adhesive Based on MPPA from Example 5

In analogy to Example 4, a light-curing adhesive with 10.9 wt.-% MMPA was prepared and the adhesive shear strength on dentine was determined. The resulting value was 22.8 MPa.

Example 7

Synthesis of 2-methacryloyloxymethyl-1,3-propylene-bisphosphonic acid

1$^{st}$ step: 2-methacryloyloxymethyl-1,3-propylene-bisphosphonic acid tetraethylester

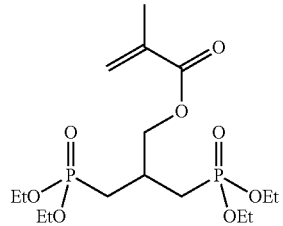 [SMILES: C=C(C)C(=O)OCC(CP(=O)(OCC)OCC)CP(=O)(OCC)OCC]

Methacrylic acid anhydride (1.45 ml, 9.7 mmol, 1.5 eq.) was added with stirring to a solution of 2-hydroxymethyl-1,3-propylene-bisphosphonic acid tetraethylester (2.24 g, 6.5 mmol), triethylamine (1.35 ml, 9.7 mmol, 1.5 eq.) and 4-(N,N-dimethylamino)-pyridine (63 mg, 0.5 mmol, 0.08 eq.) in anhydrous dichloromethane (15 ml) and the reaction mixture was subsequently heated for 6 h under reflux. Then deionized water (15 ml) was added, the organic layer was separated and the aqueous layer was extracted with dichloromethane (2×15 ml). The combined organic phases were dried with anhydrous sodium sulphate. After removal of the solvent under reduced pressure the obtained crude product was purified by column chromatography (eluent: ethyl acetate/methanol 91:9). 2.0 g (75% yield) of the product was obtained as a colorless oil.

$^1$H-NMR (400 MHz, CDCl$_3$): δ=1.31, 1.32 (2t, $^3J_{HH}$=7.1 Hz, 12H, POCH$_2$CH$_3$); 1.90-2.16 (m, 4H, CH$_2$P); 1.94 (s, 3H, CH$_3$); 2.53-2.69 (m, 1H, CHCH$_2$P); 4.04-4.17 (m, 8H, POCH$_2$CH$_3$); 4.27 (d, $^3J_{HH}$=5.1 Hz, 2H, CH$_2$OCO); 5.56-5.59 (m, 1H, CH$_2$=C); 6.10 (ls, 1H, CH$_2$=C).

$^{31}$P-NMR (162 MHz, CDCl$_3$): δ=29.3.

$^{13}$C-NMR (101 MHz, CDCl$_3$): δ=16.4 (d, $^3J_{CP}$=6.3 Hz, POCH$_2$CH$_3$); 18.4 (s, CH$_3$); 27.9 (dd, $^1J_{CP}$=141.1 Hz, $^3J_{CP}$=10.5 Hz, CH$_2$P); 28.9 (t, $^2J_{CP}$=3.9 Hz, CHCH$_2$P); 61.7 (d, $^2J_{CP}$=7.7 Hz, POCH$_2$CH$_3$); 66.9 (t, $^3J_{CP}$=9.2 Hz, CH$_2$OCO); 125.8 (s, CH$_2$=C); 136.1 (s, CH$_2$=C); 166.9 (s, C=O).

2nd step: 2-methacryloyloxymethyl-1,3-propylene-bisphosphonic acid

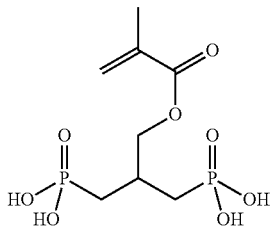 [SMILES: C=C(C)C(=O)OCC(CP(=O)(O)O)CP(=O)(O)O]

The bisphosphonate from the 1st stage (1.53 g, 3.7 mmol) was converted in analogy to the 3rd step of Example 5. 1.12 g (100% yield) of the product was obtained as a white paste.

$^1$H-NMR (400 MHz, D$_2$O): δ=1.89 (s, 3H, CH$_3$); 1.99 (dd, $^3J_{HH}$=6.8 Hz; $^2J_{HP}$=18.1 Hz, 4H, CH$_2$P); 2.43-2.58 (m, 1H, CHCH$_2$P); 4.23 (d, $^3J_{HH}$=5.0 Hz, 2H, CH$_2$OCO); 5.65-5.68 (m, 1H, CH$_2$=C); 6.11 (ls, 1H, CH$_2$=C).

$^{31}$P-NMR (162 MHz, D$_2$O): δ=29.9.

$^{13}$C-NMR (101 MHz, D$_2$O): δ=17.5 (s, CH$_3$); 28.8 (t, $^2J_{CP}$=3.8 Hz, CHCH$_2$P); 29.3 (dd, $^1J_{CP}$=135.6 Hz, $^3J_{CP}$=10.7 Hz, CH$_2$P); 67.4 (t, $^3J_{CP}$=8.8 Hz, CH$_2$OCO); 127.1 (s, CH$_2$=C); 135.9 (s, CH$_2$=C); 169.8 (s, C=O).

HRMS (m/z): calc. for C$_8$H$_{17}$O$_8$P$_2$: 303.0399; found: 303.0403 [M+H]$^+$.

Example 8

Synthesis of 2-[N-(2-methacryloyloxyethyl)-carbamoyloxymethyl]-1,3-propylene-bisphosphonic acid 1st step: 2-[N-(2-methacryloyloxyethyl)-carbamoyloxymethyl]-1,3-propylene-bisphosphonic acid tetraethylester

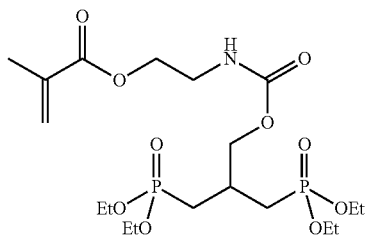 [SMILES: C=C(C)C(=O)OCCNC(=O)OCC(CP(=O)(OCC)OCC)CP(=O)(OCC)OCC]

A solution of 2-hydroxymethyl-1,3-propylene-bisphosphonic acid tetraethylester (4.8 g, 13.8 mmol) in anhydrous dichloromethane (6.0 ml) was added to a 1% solution of the tin catalyst Metatin 712 in anhydrous dichloromethane (4.0 ml). Then isocyanatoethyl-methacrylate (1.96 ml, 13.8 mmol) was added dropwise, and the reaction mixture was stirred for 3 h at room temperature. After concentrating in vacuo the obtained crude product was purified by column chromatography (eluent: ethyl acetate/methanol 95:5). 6.0 g (86% yield) of the product was obtained as a colorless oil.

$^1$H-NMR (400 MHz, CDCl$_3$): δ=1.31, 1.32 (2t, $^3J_{HH}$=7.1 Hz, 12H, POCH$_2$CH$_3$); 1.85-2.12 (m, 4H, CH$_2$P); 1.94 (s, 3H, CH$_3$); 2.43-2.62 (m, 1H, CHCH$_2$P); 3.48 (dt, $^3J_{HH}$=5.4 Hz, $^3J_{HH}$=5.4 Hz, 2H, CH$_2$NH); 4.03-4.16 (m, 8H, POCH$_2$CH$_3$); 4.19 (d, $^3J_{HH}$=5.2 Hz, 2H, CH$_2$OCONH); 4.22 (t, $^3J_{HH}$=5.4 Hz, 2H, NHCH$_2$CH$_2$O); 5.07 (t, $^3J_{HH}$=5.4 Hz, 1H, NH); 5.58-5.62 (m, 1H, CH$_2$=C); 6.12 (ls, 1H, CH$_2$=C).

$^{31}$P-NMR (162 MHz, CDCl$_3$): δ=29.5.

$^{13}$C-NMR (101 MHz, CDCl$_3$): δ=16.4 (d, $^3J_{CP}$=6.1 Hz, POCH$_2$CH$_3$); 18.3 (s, CH$_3$); 27.8 (dd, $^1J_{CP}$=141.2 Hz, $^3J_{CP}$=10.2 Hz, CH$_2$P); 29.1 (t, $^2J_{CP}$=3.9 Hz, CHCH$_2$P); 40.2 (s, CH$_2$NH); 61.7 (2d, $^2J_{CP}$=6.8 Hz, POCH$_2$CH$_3$); 63.7 (s, NHCH$_2$CH$_2$O); 67.3 (t, $^3J_{CP}$=9.4 Hz, CH$_2$OCONH); 126.1 (s, CH$_2$=C); 136.0 (s, CH$_2$=C); 156.2 (s, NHCO); 167.3 (s, C=O).

2nd step: 2-[N-(2-methacryloyloxyethyl)-carbamoyloxymethyl]-1,3-propylene-bisphosphonic acid

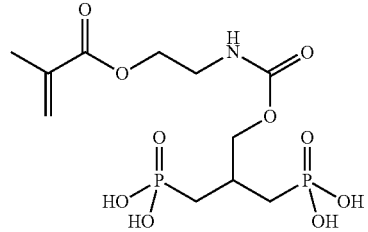 [SMILES: C=C(C)C(=O)OCCNC(=O)OCC(CP(=O)(O)O)CP(=O)(O)O]

The bisphosphonate from the 1st stage (1.85 g, 3.69 mmol) was converted in analogy to the 3rd step of Example 5. 1.34 g (93% yield) of the product was obtained as a highly viscous oil.

$^1$H-NMR (400 MHz, MeOD): δ=1.90-2.10 (m, 4H, CH$_2$P); 1.93 (s, 3H, CH$_3$); 2.42-2.62 (m, 1H, CHCH$_2$P); 3.40 (t, $^3J_{HH}$=5.4 Hz, 2H, CH$_2$NH); 4.14-4.22 (m, 4H, CH$_2$OCONH and NHCH$_2$CH$_2$O); 5.63 (ls, 1H, CH$_2$=C); 6.12 (ls, 1H, CH$_2$=C).

$^{31}$P-NMR (162 MHz, MeOD): δ=28.1.

$^{13}$C-NMR (101 MHz, MeOD): δ=18.5 (s, CH$_3$); 30.3 (dd, $^1J_{CP}$=138.1 Hz, $^3J_{CP}$=9.7 Hz, CH$_2$P); 30.8 (t, $^2J_{CP}$=3.3 Hz, CHCH$_2$P); 40.8 (s, CH$_2$NH); 64.7 (s, NHCH$_2$CH$_2$O); 68.5 (t, $^3J_{CP}$=9.8 Hz, CH$_2$OCONH); 126.6 (s, CH$_2$=C); 137.6 (s, CH$_2$=C); 158.9 (s, NHCO); 168.8 (s, C=O).

HRMS (m/z): calc. for C$_{11}$H$_{22}$NO$_{10}$P$_2$: 390.0719; found: 390.0722 [M+H]$^+$.

Example 9

Synthesis of 2-[N-(10-methacryloyloxydecyl)-carbamoyloxymethyl]-1,3-propylene-bisphosphonic acid 1st step: 10-bromodecylmethacrylate

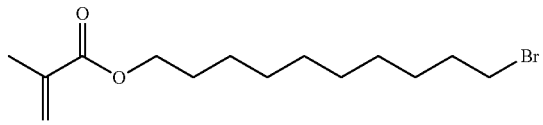 [SMILES: C=C(C)C(=O)OCCCCCCCCCCBr]

2,4,6-Collidin (12.3 ml, 92.7 mmol, 1.1 eq.) was added to a solution of 10-bromodecanol (20.0 g, 84.3 mmol) in anhydrous dichloromethane (200 ml). After cooling the mixture to 0° C. methacrylic acid chloride (16.5 ml, 168.6 mmol, 2 eq.) was slowly added dropwise and the reaction mixture was stirred for 1 h at 0° C. and at for 15 h room temperature. The reaction mixture was then washed with water (100 ml) and cold 1N HCl (100 ml). The combined organic phases were dried with anhydrous sodium sulphate. After removal of the solvent under reduced pressure the obtained crude product was purified by column chromatography (eluent: hexane/dichloromethane 8:2). 18.0 g (70% yield) of the product was obtained as a colorless liquid.

$^1$H-NMR (400 MHz, CDCl$_3$): δ=1.26-1.47 (m, 12H, CH$_2$); 1.67 (qt, $^3$J$_{HH}$=7.5 Hz, 2H, CH$_2$); 1.85 (qt, $^3$J$_{HH}$=7.5 Hz, 2H, CH$_2$); 1.94 (s, 3H, CH$_3$); 3.40 (t, $^3$J$_{HH}$=6.8 Hz, 2H, CH$_2$Br); 4.14 (t, $^3$J$_{HH}$=6.7 Hz, 2H, CH$_2$O); 5.53-5.56 (m, 1H, CH$_2$=C); 6.01 (ls, 1H, CH$_2$=C).

$^{13}$C-NMR (101 MHz, CDCl$_3$): δ=18.3 (s, CH$_3$); 25.9 (s, CH$_2$); 28.1 (s, CH$_2$); 28.6 (s, CH$_2$); 28.7 (s, CH$_2$); 29.2 (s, CH$_2$); 29.3 (s, CH$_2$); 29.4 (s, CH$_2$); 32.8 (s, CH$_2$); 33.9 (s, CH$_2$Br); 64.7 (s, CH$_2$O); 125.1 (s, CH$_2$=C); 136.5 (s, CH$_2$=C); 167.4 (s, C=O).

2$^{nd}$ step: 2-[N-(10-methacryloyloxydecyl)-carbamoyloxymethyl]-1,3-propylene-bisphosphonic acid tetraethylester

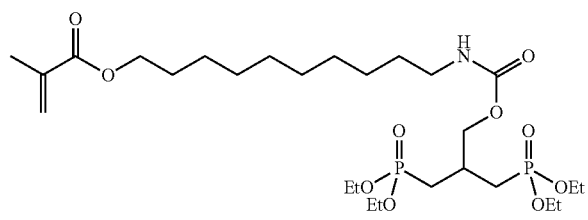 [SMILES: C=C(C)C(=O)OCCCCCCCCCCNC(=O)OCC(CP(=O)(OCC)OCC)CP(=O)(OCC)OCC]

KOCN (3.33 g, 41.0 mmol, 5.85 eq.) and Bu$_4$NBr (1.77 g, 5.49 mmol, 0.8 eq.) were added to a solution of the 10-bromodecylmethacrylate from the 1$^{st}$ step (8.36 g, 27.4 mmol, 3.9 eq.) in anhydrous acetonitrile (55 ml) and the reaction mixture was stirred for 64 h. The reaction mixture was subsequently concentrated in vacuo and hexane (100 ml) was added. After filtration of the obtained solution and concentrating in vacuo 4.75 g of a yellow oil was obtained. To this oil a solution of 2-hydroxymethyl-1,3-propylene-bisphosphonic acid tetraethylester (2.41 g, 7.0 mmol) in anhydrous dichloromethane (2.0 ml) and a 1% solution of Metatin 712 in dichloromethane (2.0 ml) were added and the reaction mixture was stirred for 15 h at room temperature. After concentrating in vacuo the obtained crude product was purified by column chromatography (eluent: ethyl acetate/methanol 95:5). 3.85 g (90% yield) of the product was obtained as a colorless oil.

$^1$H-NMR (400 MHz, CDCl$_3$): δ=1.23-1.40 (m, 12H, CH$_2$); 1.31, 1.32 (2t, $^3$J$_{HH}$=7.1 Hz, 12H, POCH$_2$CH$_3$); 1.42-1.53 (m, 2H, CH$_2$); 1.66 (qt, $^3$J$_{HH}$=6.7 Hz, 2H, CH$_2$); 1.85-2.12 (m, 4H, CH$_2$P); 1.94 (s, 3H, CH$_3$); 2.42-2.62 (m, 1H, CHCH$_2$P); 3.14 (dt, $^3$J$_{HH}$=6.6 Hz, $^3$J$_{HH}$=6.6 Hz, 2H, CH$_2$NH); 4.03-4.15 (m, 10H, POCH$_2$CH$_3$ und CH$_2$CH$_2$O); 4.16 (d, $^3$J$_{HH}$=5.2 Hz, 2H, CH$_2$OCONH); 4.73 (t, $^3$J$_{HH}$=6.6 Hz, 1H, NH); 5.52-5.55 (m, 1H, CH$_2$=C); 6.09 (ls, 1H, CH$_2$=C).

$^{31}$P-NMR (162 MHz, CDCl$_3$): δ=29.6.

$^{13}$C-NMR (101 MHz, CDCl$_3$): δ=16.4 (d, $^3$J$_{CP}$=6.1 Hz, POCH$_2$CH$_3$); 18.3 (s, CH$_3$); 26.0 (s, CH$_2$); 26.8 (s, CH$_2$); 27.8 (dd, $^1$J$_{CP}$=140.8 Hz, $^3$J$_{CP}$=10.0 Hz, CH$_2$P); 28.6 (s, CH$_2$); 29.2 (t, $^2$J$_{CP}$=4.1 Hz, CHCH$_2$P); 29.2 (s, CH$_2$); 29.3 (2s, 2CH$_2$); 29.4 (s, CH$_2$); 30.0 (s, CH$_2$); 41.1 (s, CH$_2$NH); 61.7 (2d, $^2$J$_{CP}$=6.4 Hz, POCH$_2$CH$_3$); 64.8 (s, CH$_2$CH$_2$O); 67.0 (t, $^3$J$_{CP}$=9.4 Hz, CH$_2$OCONH); 125.2 (s, CH$_2$=C); 136.7 (s, CH$_2$=C); 156.3 (s, NHCO); 167.6 (s, C=O).

3$^{rd}$ step: 2-[N-(10-methacryloyloxydecyl)-carbamoyloxymethyl]-1,3-propylene-bisphosphonic acid tetraethylester

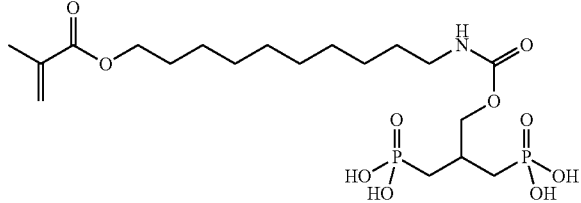 [SMILES: C=C(C)C(=O)OCCCCCCCCCCNC(=O)OCC(CP(=O)(O)O)CP(=O)(O)O]

The bisphosphonate from the 2$^{nd}$ stage (2.27 g, 3.7 mmol) was converted in analogy to the 3$^{rd}$ step of Example 5. 1.78 g (96% yield) of the product was obtained as a weakly orange solid.

$^1$H-NMR (400 MHz, MeOD): δ=1.28-1.43 (m, 12H, CH$_2$); 1.44-1.54 (m, 2H, CH$_2$); 1.67 (qt, $^3$J$_{HH}$=6.9 Hz, 2H, CH$_2$); 1.92 (s, 3H, CH$_3$); 1.94-2.10 (m, 4H, CH$_2$P); 2.43-2.61 (m, 1H, CHCH$_2$P); 3.08 (t, $^3$J$_{HH}$=7.1 Hz, 2H, CH$_2$NH); 4.13 (t, $^3$J$_{HH}$=6.6 Hz, 2H, CH$_2$CH$_2$O); 4.17 (d, $^3$J$_{HH}$=5.4 Hz, 2H, CH$_2$OCONH); 5.58-5.62 (m, 1H, CH$_2$=C); 6.07 (ls, 1H, CH$_2$=C).

$^{31}$P-NMR (162 MHz, MeOD): δ=27.9.

$^{13}$C-NMR (101 MHz, MeOD): δ=18.4 (s, CH$_3$); 27.1 (s, CH$_2$); 27.9 (s, CH$_2$); 29.7 (s, CH$_2$); 30.3 (dd, $^1$J$_{CP}$=137.2 Hz, $^3$J$_{CP}$=10.0 Hz, CH$_2$P); 30.3 (s, CH$_2$); 30.4 (s, CH$_2$); 30.6 (2s, 2CH$_2$); 30.8 (t, $^2$J$_{CP}$=3.5 Hz, CHCH$_2$P); 31.0 (s, CH$_2$); 41.9 (s, CH$_2$NH); 66.0 (s, CH$_2$CH$_2$O); 68.5 (t, $^3$J$_{CP}$=9.3 Hz, CH$_2$OCONH); 126.0 (s, CH$_2$=C); 137.9 (s, CH$_2$=C); 158.9 (s, NHCO); 168.9 (s, C=O).

HRMS (m/z): calc. for C$_{19}$H$_{38}$NO$_{10}$P$_2$: 502.1971; found: 502.1952 [M+H]$^+$.

Example 10

Synthesis of 2-(2-ethoxycarbonyl-propene-3-yloxymethyl)-1,3-propylene-bisphosphonic acid 1$^{st}$ step: 2-(2-ethoxycarbonyl-propene-3-yloxymethyl)-1,3-propylene-bisphosphonic acid tetraethylester

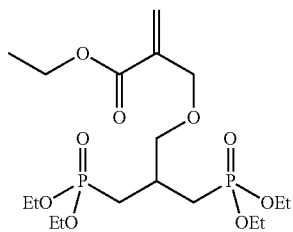 [SMILES: C=C(COCC(CP(=O)(OCC)OCC)CP(=O)(OCC)OCC)C(=O)OCC]

Ethyl-2-(chloromethyl)-acrylate (3.86 g, 26.0 mmol, 1.5 eq.) was added to a solution of 2-hydroxymethyl-1,3-propylene-bisphosphonic acid tetraethylester (6.0 g, 17.3 mmol) and triethylamine (3.62 ml, 26 mmol, 1.5 eq.) in anhydrous THF (30 ml), and the reaction mixture was stirred for 45 h at 70° C. After concentrating in vacuo deionized water (50 ml)

was added and the obtained solution was extracted with ethylacetate (3×50 ml). The combined organic phases were dried with anhydrous sodium sulphate. After removal of the solvent under reduced pressure the obtained crude product was purified by column chromatography (eluent: ethylacetate/methanol 98:2). 3.77 g (48% yield) of the product was obtained as a yellowish oil.

$^1$H-NMR (400 MHz, CDCl$_3$): δ=1.28 (t, $^3J_{HH}$=7.9 Hz, 3H, COOCH$_2$CH$_3$); 1.30 (t, $^3J_{HH}$=7.8 Hz, 12H, POCH$_2$CH$_3$); 1.92-2.10 (m, 4H, CH$_2$P); 2.37-2.53 (m, 1H, CHCH$_2$O); 3.60 (d, $^3J_{HH}$=5,1 Hz, 2H, CHCH$_2$O); 4.00-4.15 (m, 8H, POCH$_2$CH$_3$); 4.17 (s, 2H, OCH$_2$C); 4.20 (q, $^3J_{HH}$=7.1 Hz, 2H, COOCH$_2$CH$_3$); 5.81 (s, 1H, CH$_2$=C); 6.26 (s, 1H, CH$_2$=C).

$^{31}$P-NMR (162 MHz, CDCl$_3$): δ=30.3.

$^{13}$C-NMR (101 MHz, CDCl$_3$): δ=14.2 (s, COOCH$_2$CH$_3$); 16.4 (d, $^3J_{CP}$=5.7 Hz, POCH$_2$CH$_3$); 27.8 (dd, $^1J_{CP}$=140.2 Hz, $^3J_{CP}$=10.7 Hz, CH$_2$P); 29.7 (t, $^2J_{CP}$=3.7 Hz, CHCH$_2$O); 60.7 (s, COOCH$_2$CH$_3$); 61.5 (2d, $^2J_{CP}$=6.6 Hz, POCH$_2$CH$_3$); 69.1 (s, CH$_2$=CCH$_2$O); 73.1 (t, $^3J_{CP}$=8.6 Hz, CHCH$_2$O); 125.4 (s, CH$_2$=C); 137.4 (s, CH$_2$=C); 165.8 (s, C=O).

2$^{nd}$ step: 2-(2-ethoxycarbonyl-propene-3-yloxymethyl)-1,3-propylene-bisphosphonic acid

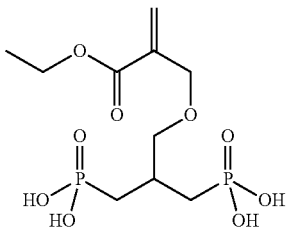 [SMILES: C=C(COCC(CP(=O)(O)O)CP(=O)(O)O)C(=O)OCC]

The bisphosphonate from the 1$^{st}$ stage (1.69 g, 3.7 mmol) was converted in analogy to the 3$^{rd}$ step of Example 5. 1.28 g (100% yield) of the product was obtained as a highly viscous oil.

$^1$H-NMR (400 MHz, D$_2$O): δ=1.27 (t, $^3J_{HH}$=7.1 Hz, 3H, COOCH$_2$CH$_3$); 1.87-2.04 (m, 4H, CH$_2$P); 2.30-2.45 (m, 1H, CHCH$_2$O); 3.59 (d, $^3J_{HH}$=5.7 Hz, 2H, CHCH$_2$O); 4.23 (q, $^3J_{HH}$=7.1 Hz, 2H, COOCH$_2$CH$_3$); 4.25 (s, 2H, OCH$_2$C); 5.94 (s, 1H, CH$_2$=C); 6.35 (s, 1H, CH$_2$=C).

$^{31}$P-NMR (162 MHz, D$_2$O): δ=28.4.

$^{13}$C-NMR (101 MHz, D$_2$O): δ=13.3 (s, COOCH$_2$CH$_3$); 28.8 (dd, $^1J_{CP}$=134.5 Hz, $^3J_{CP}$=9.6 Hz, CH$_2$P); 29.1 (t, $^2J_{CP}$=2.9 Hz, CHCH$_2$O); 62.0 (s, COOCH$_2$CH$_3$); 69.3 (s, CH$_2$=CCH$_2$O); 72.6 (t, $^3J_{CP}$=9.2 Hz, CHCH$_2$O); 129.6 (s, CH$_2$=C); 136.2 (s, CH$_2$=C); 168.1 (s, C=O).

HRMS (m/z): calc. for C$_{10}$H$_{21}$O$_9$P$_2$: 347.0661; found: 347.0664 [M+H]$^+$.

Example 11

Synthesis of 2-(N-butyl-acrylamidomethyl)-1,3-propylene-bisphosphonic acid

1$^{st}$ step: 2-(Methanesulfonyloxymethyl)-1,3-propylene-bisphosphonic acid tetraethylester

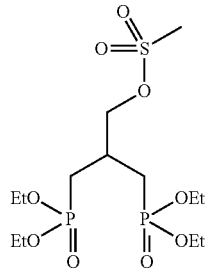 [SMILES: CCOP(=O)(CC(COS(C)(=O)=O)CP(=O)(OCC)OCC)OCC]

Methanesulfonylchloride (2.2 ml, 28.6 mmol) was added dropwise at 0° C. to a solution of 2-hydroxymethyl-1,3-propylene-bisphosphonic acid tetraethylester (9.0 g, 26.0 mmol) and triethylamine (4.0 ml, 28.6 mmol, 1.1 eq.) in anhydrous dichloromethane (90 ml). The reaction mixture was stirred for 30 min at 0° C. and for 2 h at room temperature. After concentrating in vacuo deionized water (100 ml) was added and the mixture was extracted with ethylacetate (3×100 ml). The combined organic phases were dried with anhydrous sodium sulphate. After removal of the solvent under reduced pressure the obtained crude product was purified by column chromatography (eluent: ethylacetate/methanol 9:1). 9.37 g (85% yield) of the product was obtained as a colorless oil.

$^1$H-NMR (400 MHz, CDCl$_3$): δ=1.33 (t, $^3J_{HH}$=7.1 Hz, 12H, POCH$_2$CH$_3$); 1.89-2.14 (m, 4H, CH$_2$P); 2.51-2.69 (m, 1H, CHCH$_2$P); 3.06 (s, 3H, CH$_3$S); 4.04-4.16 (m, 8H, POCH$_2$CH$_3$); 4.42 (d, $^3J_{HH}$=4.5 Hz, 2H, CH$_2$OS).

$^{31}$P-NMR (162 MHz, CDCl$_3$): δ=28.4.

$^{13}$C-NMR (101 MHz, CDCl$_3$): δ=16.4 (d, $^3J_{CP}$=6.3 Hz, POCH$_2$CH$_3$); 27.5 (dd, $^1J_{CP}$=141.0 Hz, $^3J_{CP}$=11.3 Hz, CH$_2$P); 29.3 (t, $^2J_{CP}$=3.9 Hz, CHCH$_2$P); 37.1 (s, CH$_3$S); 61.8, 61.9 (2d, $^2J_{CP}$=6.5 Hz, POCH$_2$CH$_3$); 72.1 (t, $^3J_{CP}$=8.1 Hz, CH$_2$OS).

2$^{nd}$ step: 2-(N-butyl-aminomethyl)-1,3-propylene-bisphosphonic acid tetraethylester

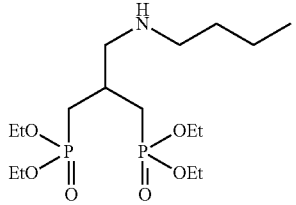 [SMILES: CCCCNCC(CP(=O)(OCC)OCC)CP(=O)(OCC)OCC]

A solution of butylamine (20.6 ml, 209 mmol, 10 eq.) in EtOH (110 ml) was added to the mesylate from the 1$^{st}$ step (8.85 g, 20.9 mmol), and the reaction mixture was stirred for 50 h at 60° C. After concentrating the reaction mixture in vacuo deionized water (50 ml) was added, and the mixture was adjusted to a pH value of >11 with 10% aqueous NaOH and extracted with dichloromethane (3×60 ml). The combined organic phases were dried with anhydrous sodium sulphate and the solvent was removed under reduced pressure. 7.0 g (84% yield) of the product was obtained as a yellow oil and used for the next step without further purification.

$^1$H-NMR (400 MHz, CDCl$_3$): δ=0.90 (t, $^3J_{HH}$=7.3 Hz, 3H, CH$_2$CH$_2$CH$_3$); 1.27-1.37 (m, 2H, CH$_2$); 1.32 (t, $^3J_{HH}$=7.0 Hz, 12H, POCH$_2$CH$_3$); 1.37-1.48 (m, 2H, CH$_2$); 1.94-2.10 (m, 4H, CH$_2$P); 2.22-2.39 (m, 1H, CHCH$_2$P); 2.57 (t, $^3J_{HH}$=7.2 Hz, 2H, CH$_2$CH$_2$N); 2.74 (d, $^3J_{HH}$=6.1 Hz, 2H, CHCH$_2$N); 4.01-4.17 (m, 8H, POCH$_2$CH$_3$).

$^{31}$P-NMR (162 MHz, CDCl$_3$): δ=30.9.

$^{13}$C-NMR (101 MHz, CDCl$_3$): δ=14.0 (s, CH$_2$CH$_2$CH$_3$); 16.4 (d, $^3J_{CP}$=5.4 Hz, POCH$_2$CH$_3$); 20.5 (s, CH$_2$); 28.6 (dd, $^1J_{CP}$=139.0 Hz, $^3J_{CP}$=9.6 Hz, CH$_2$P); 29.5 (t, $^2J_{CP}$=3.9 Hz, CHCH$_2$P); 32.4 (s, CH$_2$); 49.7 (s, CH$_2$CH$_2$N); 53.9 (t, $^3J_{CP}$=8,8 Hz, CHCH$_2$N); 61.4, 61.5 (2d, $^2J_{CP}$=6.5 Hz, POCH$_2$CH$_3$).

3rd step: 2-(N-butyl-acrylamidomethyl)-1,3-propylene-bisphosphonic acid tetraethylester

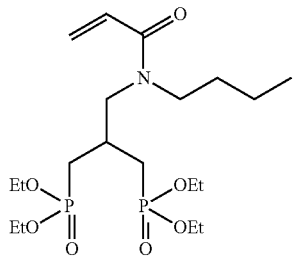 [SMILES: C=CC(=O)N(CCCC)CC(CP(=O)(OCC)OCC)CP(=O)(OCC)OCC]

The aminophosphonate from the 2nd step (6.93 g, 17.3 mmol) and triethylamine (2.65 ml, 19.0 mmol, 1.1 eq.) were diluted with dry dichlormethane (40 ml) and cooled to 0° C. A solution of acrylic acid chloride (1.41 ml, 17.3 mmol, 1 eq.) in dry dichlormethane (25 ml) was added dropwise to the obtained mixture and the reaction mixture was stirred for 30 min at 0° C. and for 2 h at room temperature. The reaction mixture was then washed with 10% aqueous NaOH (2×25 ml) and the aqueous phases were extracted with ethylacetate (3×50 ml). The combined organic phases were dried with anhydrous sodium sulphate. After removal of the solvent under reduced pressure the obtained crude product was purified by column chromatography (eluent: ethylacetate/methanol 9:1). 7.0 g (89% yield) of the product was obtained as a yellow oil.

$^1$H-NMR (400 MHz, CDCl$_3$): 2 rotamers δ=0.91, 0.93 (2t, $^3J_{HH}$=7.2 Hz, 3H, CH$_2$CH$_2$CH$_3$); 1.26-1.36 (m, 2H, CH$_2$); 1.30, 1.31 (2t, $^3J_{HH}$=7.0 Hz, 12H, POCH$_2$CH$_3$); 1.50-1.63 (m, 2H, CH$_2$); 1.74-1.91 (m, 2H, CH$_2$P); 1.99-2.15 (m, 2H, CH$_2$P); 2.38-2.56 (m, 1H, CHCH$_2$P); 3.33, 3.39 (2t, $^3J_{HH}$=7.8 Hz, 2H, CH$_2$CH$_2$N); 3.56, 3.64 (2d, $^3J_{HH}$=7.5 Hz, 2H, CHCH$_2$N); 4.01-4.16 (m, 8H, POCH$_2$CH$_3$); 5.66-5.72 (m, 1H, CH$_2$=CH); 6.33, 6.36 (2dd, $^2J_{HH}$=2.0 Hz, $^3J_{HH}$=16.7 Hz, 1H, CH$_2$=CH); 6.56, 6.67 (2dd, $^3J_{HH}$=10.4 Hz, $^3J_{HH}$=16.7 Hz, 1H, CH$_2$=CH).

$^{31}$P-NMR (162 MHz, CDCl$_3$): 2 rotamers δ=29.2, 30.2.

$^{13}$C-NMR (101 MHz, CDCl$_3$): 2 rotamers δ=13.8 (2s, CH$_2$CH$_2$CH$_3$); 16.4 (d, $^3J_{CP}$=6.6 Hz, POCH$_2$CH$_3$); 20.0, 20.3 (2s, CH$_2$); 27.7 (dd, $^1J_{CP}$=140.3 Hz, $^3J_{CP}$=9.1 Hz, CH$_2$P); 28.3 (t, $^2J_{CP}$=3.9 Hz, CHCH$_2$P); 28.4 (dd, $^1J_{CP}$=139.9 Hz, $^3J_{CP}$=9.1 Hz, CH$_2$P); 29.5 (t, $^2J_{CP}$=3.9 Hz, CHCH$_2$P); 31.5 (s, CH$_2$); 47.1, 47.7 (2s, CH$_2$CH$_2$N); 49.9, 51.9 (2t, $^3J_{CP}$=9.2 Hz, CHCH$_2$N); 61.6, 61.7, 61.8 (4d, $^2J_{CP}$=6.6 Hz, POCH$_2$CH$_3$); 127.6, 127.8 (2s, CH=CH$_2$); 128.3, 128.4 (2s, CH=CH$_2$); 166.5, 167.0 (2s, C=O).

4th step: 2-(N-butyl-acrylamidomethyl)-1,3-propylene-bisphosphonic acid

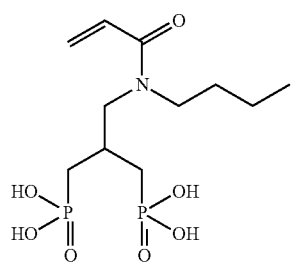 [SMILES: C=CC(=O)N(CCCC)CC(CP(=O)(O)O)CP(=O)(O)O]

The bisphosphonate from the 3rd stage (1.69 g, 3.71 mmol) was converted in analogy to the 3rd step of Example 5. 1.26 g (99% yield) of the product was obtained as a weakly yellow solid.

$^1$H-NMR (400 MHz, D$_2$O): 2 rotamers δ=0.81 (t, $^3J_{HH}$=7.4 Hz, 3H, CH$_2$CH$_2$CH$_3$); 1.16-1.28 (m, 2H, CH$_2$); 1.42-1.57 (m, 2H, CH$_2$); 1.68-1.85 (m, 2H, CH$_2$P); 1.86-2.04 (m, 2H, CH$_2$P); 2.34-2.54 (m, 1H, CHCH$_2$P); 3.33, 3.38 (2t, $^3J_{HH}$=7.7 Hz, 2H, CH$_2$CH$_2$N); 3.52, 3.56 (2d, $^3J_{HH}$=7.5 Hz, 2H, CHCH$_2$N); 5.73 (dm, $^3J_{HH}$=10.6 Hz, 1H, CH$_2$=CH); 6.11 (dm, $^3J_{HH}$=16.9 Hz, 1H, CH$_2$=CH); 6.67, 6.68 (2dd, $^3J_{HH}$=10.4 Hz, $^3J_{HH}$=16.7 Hz, 1H, CH$_2$=CH).

$^{31}$P-NMR (162 MHz, D$_2$O): 2 rotamers δ=27.6, 28.2.

$^{13}$C-NMR (101 MHz, D$_2$O): 2 rotamers δ=12.9, 13.0 (2s, CH$_2$CH$_2$CH$_3$); 19.1, 19.4 (2s, CH$_2$); 27.5, 28.5 (2t, $^2J_{CP}$=3.7 Hz, CHCH$_2$P); 28.7, 29.2 (2dd, $^1J_{CP}$=135.7 Hz, $^3J_{CP}$=9.1 Hz, CH$_2$P); 30.4 (s, CH$_2$); 46.7, 47.9 (2s, CH$_2$CH$_2$N); 50.2, 52.0 (2t, $^3J_{CP}$=9.8 Hz, CHCH$_2$N); 127.4, 127.5 (2s, CH=CH$_2$); 128.9, 129.0 (2s, CH=CH$_2$); 169.0, 169.3 (2s, C=O).

HRMS (m/z): calc. for C$_{11}$H$_{24}$NO$_7$P$_2$: 344.1028; found: 344.1043 [M+H]$^+$.

Example 12

Preparation of Light-curing Adhesives on the Basis of the Bisphosphonic Acids from Examples 5 and 7 to 11

To examine the dentine adhesion on bovine tooth dentine, adhesives having the composition given in Table 2 were prepared using the bisphosphonic acids from Examples 5 and 7 to 11:

TABLE 2

| Composition of adhesives | |
|---|---|
| Komponente | Menge (Gew.-%) |
| Bisphosphonsäure gemäβ Tabelle 3 | 24.00 |
| DEBAAP[1] | 37.70 |
| Photoinitiator[2] | 0.60 |
| BHT[3] | 0.03 |
| EtOH | 27.67 |
| Wasser | 10.00 |

[1] N,N'-Diethyl-1,3-bis(acrylamido)propan,
[2] Mischung aus Campherchinon (0.6%),
[3] 3,5-Di-tert-butyl-4-hydroxytuluol.

Freshly extracted bovine teeth were embedded in plastic cylinders in such a way that the dentine or enamel and the plastic were on one level. The surfaces of the dentine or enamel were ground with wet silicon carbide paper (120-grit and 1000-grit). A layer of adhesive of the above composition was then brushed on with a microbrush and spread for 15 s and the layer was dried with pressurized air. AdheSE-Bonding (Ivoclar Vivadent AG) was then applied with a microbrush and exposed to light for 10 s using an LED lamp (Bluephase G20, Ivoclar Vivadent AG). A composite cylinder of Tetric® Ceram (Ivoclar Vivadent) was polymerized onto the adhesive layer in two layers of 1-2 mm each. The testpieces were then stored in water for 24 h at 37° C. and the adhesive shear strength was determined according to the ISO guideline "ISO 1994-ISO TR 11405: Dental Materials Guidance on Testing of Adhesion to Tooth Structure". The results are given in Table 3 and show very good adhesive values.

TABLE 3

Adhesive shear strength of tested adhesives

| Bisphosphonic acid | Dentine SBS (MPa) | Enamel SBS (MPa) |
|---|---|---|
| Example 5 | 24.3 | 22.7 |
| Example 7 | 25.1 | 26.0 |
| Example 8 | 29.2 | 29.5 |
| Example 9 | 26.7 | 28.7 |
| Example 10 | 17.5 | 27.0 |
| Example 11 | 14.7 | 15.3 |

The invention claimed is:

1. Dental material comprising a polymerizable bisphosphonic acid of Formula III:

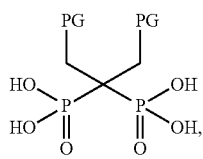

Formula III wherein
PG independently represents a polymerizable group selected from $CH_2=CR^2-CO-O-$, $CH_2=CR^2-CO-NR^3-$,
$R^2$ independently represents H or $CH_3$,
$R^3$ independently represents H or a $C_1$-$C_{10}$ alkyl radical.

2. Dental material comprising a polymerizable bisphosphonic acid of Formula V:

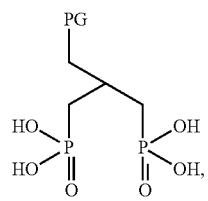

Formula V wherein
PG represents a polymerizable group selected from $CH_2=CR^2-CO-O-$, $CH_2=CR^2-CO-NR^3-$ and $R^4O-CO-C(=CH_2)-CH_2-O-$,
$R^2$ represents H or $CH_3$,
$R^3$ represents H or a $C_1$-$C_{10}$ alkyl radical,
$R^4$ represents H, a $C_1$-$C_{10}$ alkyl radical, phenyl or mesityl.

3. Dental material according to claim 2, wherein:
PG represents a polymerizable group selected from $CH_2=CR^2-CO-O-$ and $CH_2=CR^2-CO-NR^3-$,
$R^2$ represents H or $CH_3$—,
$R^3$ represents H or a $C_1$-$C_{10}$ alkyl radical.

4. Dental material according to claim 1, which comprises one or more additional radically polymerizable monomers.

5. Dental material according to claim 4, which comprises methyl, ethyl, hydroxyethyl, butyl, benzyl, tetrahydrofurfuryl or isobornyl (meth)acrylate, bisphenol-A-di(meth) acrylate, bis-GMA, UDMA, di-, tri- or tetra-ethylene glycol di(meth) acrylate, trimethylolpropane tri(meth) acrylate, pentaerythritol tetra(meth)acrylate, glycerol di(meth)acrylate, 1,4-butanediol di(meth)acrylate, 1,10-decanediol di(meth)acrylate, 1,12-dodecanediol di(meth)acrylate,
and/or
one or more N-mono- or -disubstituted acrylamides, N-ethylacrylamide, N,N-dimethacrylamide, N-(2-hydroxyethyl)acrylamide, N-methyl-N-(2-hydroxyethyl) acrylamide, one or more N-monosubstituted methacrylamides, N-ethylmethacrylamide, N-(2-hydroxyethyl) methacrylamide, N-vinylpyrrolidone, one or more cross-linking allyl ethers,
and/or
one or more cross-linking pyrrolidones, 1,6-bis(3-vinyl-2-pyrrolidonyl)-hexane, one or more cross-linking bisacrylamides, methylene or ethylene bisacrylamide, one or more cross-linking bis(meth)acrylamides, N,N'-diethyl-1,3-bis(acrylamido)-propane, 1,3-bis(methacrylamido)-propane, 1,4-bis(acrylamido)-butane, 1,4-bis(acryloyl)-piperazine,
or a mixture thereof.

6. Dental material according to claim 1, which comprises one or more additional radically polymerizable, acid group-containing monomers.

7. Dental material according to claim 6, which comprises maleic acid, acrylic acid, methacrylic acid, 2-(hydroxymethyl)acrylic acid, 4-(meth)acryloyloxyethyltrimellitic anhydride, 10-methacryloyloxydecylmalonic acid, N-(2-hydroxy-3-methacryloyloxypropyl)-N-phenylglycine, 4-vinylbenzoic acid,
and/or
vinylphosphonic acid, 4-vinylphenylphosphonic acid, 4-vinyl-benzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid, 2-[4-(dihydroxyphosphoryl)-2-oxa-butyl]-acrylic acid ethyl- or -2,4,6-trimethylphenyl ester
and/or
2-methacryloyloxypropyl mono- or dihydrogen phosphate, 2-methacryloyloxyethylphenyl hydrogen phosphate, dipentaerythritol-pentamethacryloyloxyphosphate, 10-methacryloyl-oxydecyl dihydrogen phosphate, phosphoric acid mono-(1-acryloyl-piperidine-4-yl)-ester, 6-(methacrylamido)hexyl dihydrogen phosphate, 1,3-bis-(N-acryloyl-N-propyl-amino)-propane-2-yl-dihydrogen phosphate,
and/or
vinylsulphonic acid, 4-vinylphenylsulphonic acid, 3-(meth-acrylamido)propyl sulphonic acid,
or a mixture thereof.

8. Dental material according to claim 1, which comprises an initiator for radical polymerization.

9. Dental material according to claim 1, which comprises organic and/or inorganic filler.

10. Dental material according to claim 1, which comprises
a) 0.1 to 50 wt.-%, polymerizable bisphosphonic acid of Formula I,
b) 0.01 to 10 wt.-%, initiator,
c) 0 to 80 wt.-%, co-monomer,
d) 0 to 30 wt.-%, adhesive monomer,
e) 0 to 80 wt.-% filler and
f) 0 to 70 wt.-%, solvent.

11. A method of using the dental material according to claim 10 as an adhesive which comprises adding 0 to 20 wt.-% filler to the dental material.

12. A method of using the dental material according to claim 10 as a composite which comprises adding 20 to 80 wt.-% filler to the dental material.

13. A method of using the polymerizable bisphosphonic acid of Formula III as defined in claim 1 for the preparation of a dental material.

14. A method of using the polymerizable bisphosphonic acid of Formula III according to claim 13 for the preparation of an adhesive, cement or composite.

15. A method of using the polymerizable bisphosphonic acid of Formula III according to claim 14, wherein the adhesive is self-etching.

16. A method of using the polymerizable bisphosphonic acid of Formula III according to claim 14, wherein the cement is self-etching.

17. Dental material according to claim 1, wherein
PG represents particular $CH_2=CR^2-CO-O-$,
$R^2$ represents $CH_3$.

18. Dental material according to claim 1, wherein
$R^3$ represents a $C_1$-$C_7$ radical, a $C_1$-$C_5$ radical, or a $C_1$-$C_3$.

19. Dental material according to claim 18, wherein
$R^3$ represents $CH_3$ or $C_2H_5$.

20. Dental material according to claim 2, wherein
$R^3$ represents a $C_1$-$C_7$ radical, a $C_1$-$C_5$ radical, or a $C_1$-$C_3$ radical.

21. Dental material according to claim 20, wherein
$R^3$ represents $CH_3$ or $C_2H_5$.

22. Dental material according to claim 3, wherein
$R^3$ represents a $C_1$-$C_7$ radical, a $C_1$-$C_5$ radical, or a $C_1$-$C_3$ radical.

23. Dental material according to claim 22, wherein
$R^3$ represents $CH_3$ or $C_2H_5$.

24. Dental material according to claim 10, which comprises
a) 1 to 40 wt.-%, polymerizable bisphosphonic acid of Formula I,
b) 0.1 to 3 wt.-% initiator,
c) 0 to 60 wt.-% co-monomer,
d) preferably 0.5 to 15 wt.-% adhesive monomer,
e) 0 to 80 wt.-% filler and
f) 0 to 60 wt.-% solvent.

25. Dental material according to claim 10, which comprises
a) 2 to 30 wt.-% polymerizable bisphosphonic acid of Formula I,
b) 0.2 to 2 wt.-% initiator,
c) 5 to 50 wt.-% co-monomer,
d) 1 to 5 wt.-% adhesive monomer,
e) 0 to 80 wt.-% filler and
f) 0 to 50 wt.-% solvent.

26. Dental material according to claim 10, which comprises
a) 5 to 20 wt.-% polymerizable bisphosphonic acid of Formula I,
b) 0.2 to 2 wt.-% initiator,
c) 5 to 50 wt.-% co-monomer,
d) 1 to 5 wt.-% adhesive monomer,
e) 0 to 80 wt.-% filler and
f) 0 to 50 wt.-% solvent.

27. Dental material according to claim 2, wherein
PG represents a polymerizable group selected from $CH_2=CR^2-CO-O-$ and $CH_2=CR^2-CO-NR^3-$.

28. Dental material according to claim 2, which comprises one or more additional radically polymerizable monomers.

29. Dental material according to claim 28, which comprises methyl, ethyl, hydroxyethyl, butyl, benzyl, tetrahydrofurfuryl or isobornyl (meth)acrylate, bisphenol-A-di(meth)acrylate, bis-GMA, UDMA, di-, tri- or tetra-ethylene glycol di(meth) acrylate, trimethylolpropane tri(meth)acrylate, pentaerythritol tetra(meth)acrylate, glycerol di(meth)acrylate, 1,4-butanediol di(meth)acrylate, 1,10-decanediol di(meth)acrylate, 1,12-dodecanediol di(meth)acrylate,
and/or
one or more N-mono- or -disubstituted acrylamides, N-ethylacrylamide, N,N-dimethacrylamide, N-(2-hydroxyethyl)acrylamide, N-methyl-N-(2-hydroxyethyl)acrylamide, one or more N-monosubstituted methacrylamides, N-ethylmethacrylamide, N-(2-hydroxyethyl)methacrylamide, N-vinylpyrrolidone, one or more cross-linking allyl ethers,
and/or
one or more cross-linking pyrrolidones, 1,6-bis(3-vinyl-2-pyrrolidonyl)-hexane, one or more cross-linking bisacryl-amides, methylene or ethylene bisacrylamide, one or more cross-linking bis(meth)acrylamides, N,N'-diethyl-1,3-bis-(acrylamido)-propane, 1,3-bis(methacrylamido)-propane, 1,4-bis(acrylamido)-butane, 1,4-bis(acryloyl)-piperazine,
or a mixture thereof.

30. Dental material according to claim 2, which comprises one or more additional radically polymerizable, acid group-containing monomers.

31. Dental material according to claim 30, which comprises
maleic acid, acrylic acid, methacrylic acid, 2-(hydroxymethyl)acrylic acid, 4-(meth)acryloyloxyethyltrimellitic anhydride, 10-methacryloyloxydecylmalonic acid, N-(2-hydroxy-3-methacryloyloxypropyl)-N-phenylglycine, 4-vinylbenzoic acid,
and/or
vinylphosphonic acid, 4-vinylphenylphosphonic acid, 4-vinyl-benzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid, 2-[4-(dihydroxyphosphoryl)-2-oxa-butyl]-acrylic acid ethyl- or -2,4,6-trimethylphenyl ester
and/or
2-methacryloyloxypropyl mono- or dihydrogen phosphate, 2-methacryloyloxyethylphenyl hydrogen phosphate, dipenta-erythritol-pentamethacryloyloxyphosphate, 10-methacryloyl-oxydecyl dihydrogen phosphate, phosphoric acid mono-(1-acryloyl-piperidine-4-yl)-ester, 6-(methacrylamido)hexyl dihydrogen phosphate, 1,3-bis-(N-acryloyl-N-propyl-amino)-propane-2-yl-dihydrogen phosphate,
and/or
vinylsulphonic acid, 4-vinylphenylsulphonic acid, 3-(methacrylamido)propyl sulphonic acid,
or a mixture thereof.

32. Dental material according to claim 2, which comprises an initiator for radical polymerization.

33. Dental material according to claim 2, which comprises organic and/or inorganic filler.

34. Dental material according to claim 2, which comprises
a) 0.1 to 50 wt.-%, polymerizable bisphosphonic acid of Formula I,
b) 0.01 to 10 wt.-%, initiator,
c) 0 to 80 wt.-%, co-monomer,
d) 0 to 30 wt.-%, adhesive monomer,
e) 0 to 80 wt.-% filler and
f) 0 to 70 wt.-%, solvent.

35. A method of using the dental material according to claim 34 as an adhesive which comprises adding 0 to 20 wt.-% filler to the dental material.

36. A method of using the dental material according to claim 34 as a composite which comprises adding 20 to 80 wt.-% filler to the dental material.

37. A method of using the polymerizable bisphosphonic acid of Formula V as defined in claim 2 for the preparation of a dental material.

38. A method of using the polymerizable bisphosphonic acid of Formula V according to claim 37 for the preparation of an adhesive, cement or composite.

39. A method of using the polymerizable bisphosphonic acid of Formula V according to claim 38, wherein the adhesive is self-etching.

40. A method of using the polymerizable bisphosphonic acid of Formula V according to claim 38, wherein the cement is self-etching.

41. Dental material according to claim 34, which comprises
 a) 1 to 40 wt.-%, polymerizable bisphosphonic acid of Formula I,
 b) 0.1 to 3 wt.-% initiator,
 c) 0 to 60 wt.-% co-monomer,
 d) preferably 0.5 to 15 wt.-% adhesive monomer,
 e) 0 to 80 wt.-% filler and
 f) 0 to 60 wt.-% solvent.

42. Dental material according to claim 34, which comprises
 a) 2 to 30 wt.-% polymerizable bisphosphonic acid of Formula I,
 b) 0.2 to 2 wt.-% initiator,
 c) 5 to 50 wt.-% co-monomer,
 d) 1 to 5 wt.-% adhesive monomer,
 e) 0 to 80 wt.-% filler and
 f) 0 to 50 wt.-% solvent.

43. Dental material according to claim 34, which comprises
 a) 5 to 20 wt.-% polymerizable bisphosphonic acid of Formula I,
 b) 0.2 to 2 wt.-% initiator,
 c) 5 to 50 wt.-% co-monomer,
 d) 1 to 5 wt.-% adhesive monomer,
 e) 0 to 80 wt.-% filler and
 f) 0 to 50 wt.-% solvent.

* * * * *